(12) United States Patent
Lin

(10) Patent No.: US 9,801,840 B1
(45) Date of Patent: Oct. 31, 2017

(54) PHARMACEUTICAL COMPOSITION AND USE THEREOF

(71) Applicant: National Taiwan Normal University, Taipei (TW)

(72) Inventor: Jung-Yaw Lin, Taipei (TW)

(73) Assignee: National Taiwan National University, Taipei (TW)

( * ) Notice: Subject to any disclaimer, the term of this patent is extended or adjusted under 35 U.S.C. 154(b) by 0 days.

(21) Appl. No.: 15/143,894

(22) Filed: May 2, 2016

(51) Int. Cl.
*A61K 31/191* (2006.01)
*A61K 31/4418* (2006.01)

(52) U.S. Cl.
CPC ........ *A61K 31/191* (2013.01); *A61K 31/4418* (2013.01)

(58) Field of Classification Search
None
See application file for complete search history.

(56) References Cited

PUBLICATIONS

Horlad et al., Molecular Nutrition & Food Reserch (2013), 57(6), pp. 1046-1054.*
Al-Assaf, African Journal of Biotechnology (2013), 12(19), pp. 2733-2742.*
CAPLUS in STN, Acc. No. 2013:262208, Horlad et al, Molecular Nutrition & Food Research (2013), 57(6), pp. 1046-1054 (abstract).*
CAPLUS in STN, Acc. No. 2013:946901, Al-Assaf, African Journal of Biochemistry (2013), 12(19), pp. 2733-2742 (abstract).*
Ku et al., "Corosolic acid inhibits hepatocellular carcinoma cell migration by targeting the VEGFR2/Src/FAK pathway," PLoS One. 10(5): e0126725 (17 pages) May 15, 2015.
Olsson AK, Dimberg A, Kreuger J, Claesson-Welsh L., "VEGF receptor signalling-in control of vascular function," Nat. Rev. Mol. Cell Biol., 2006, 7(5):359-371.
Claesson-Welsh L, Welsh M., "VEGFA and tumour angiogenesis," J. Intern. Med., 2013, 273(2):114-127.
Lamalice L, HouleFo, Huot J., "Phosphorylation of Tyr1214 within VEGFR-2 Triggers the Recruitment of Nck and Activation of Fyn Leading to SAPK2/p38 Activation and Endothelial Cell Migration in Response to VEGF," J. Biol. Chem., 2006, 281(45):34009-34020.
Zhang L, Wang JN, Tang JM, Kong X, Yang JY, Zheng F, et al., VEGF is essential for the growth and migration of human hepatocellular carcinoma cells, Mol. Biol. Rep., 2012, 39(5):5085-5093.
Lee K, Jeong KW, Lee Y, Song JY, Kim MS, Lee GS, et al., "Pharmacophore modeling and virtual screening studies for new VEGFR-2 kinase inhibitors," Eur. J. Med. Chem., 2010, 45(11):5420-5427.
Llovet JM, Ricci S, Mazzaferro V, Hilgard P, Gane E, Blanc JF, et al., "Sorafenib in advanced hepatocellular carcinoma," N. Engl. J. Med., 2008, 359(4):378-390.
Zhu AX, Duda DG, Sahani DV, Jain RK, "HCC and angiogenesis: possible targets and future directions," Nat. Rev. Clin. Oncol., 2011, 8(5):292-301.
Kim JH, Kim YH, Song GY, Kim DE, Jeong YJ, Liu KH, et al., "Ursolic acid and its natural derivative corosolic acid suppress the proliferation of APC-mutated colon cancer cells through promotion of ?-catenin degradation," Food Chem. Toxicol., 2014, 67:87-95.
Matsumoto T, Claesson-Welsh L., "VEGF receptor signal transduction," Sci. STKE, 2001, 2001(112):re21.
Roskoski R, Jr., "VEGF receptor protein-tyrosine kinases: structure and regulation," Biochem. Biophys. Res. Commun., 2008, 375(3):287-291.
Gottwein JM, Jensen SB, Li YP, Ghanem L, Scheel TKH, Serre SBN, et al. "Combination treatment with hepatitis C virus protease and NS5A inhibitors is effective against recombinant genotype 1a, 2a, and3a Viruses," Antimicrob. Agents Chemother., 2013, 57(3)1291-1303.

* cited by examiner

Primary Examiner — Brian J Davis
(74) Attorney, Agent, or Firm — McCarter & English, LLP; Yu Lu

(57) ABSTRACT

The present invention provides a pharmaceutical composition including a therapeutically efficient amount of a compound represented by formula (1), at least an anticancer agent, and a pharmaceutically acceptable carrier. The present invention further provides a use of the compound represented by formula (1) for the manufacture of a medicament for treating hepatocellular carcinoma.

18 Claims, 28 Drawing Sheets

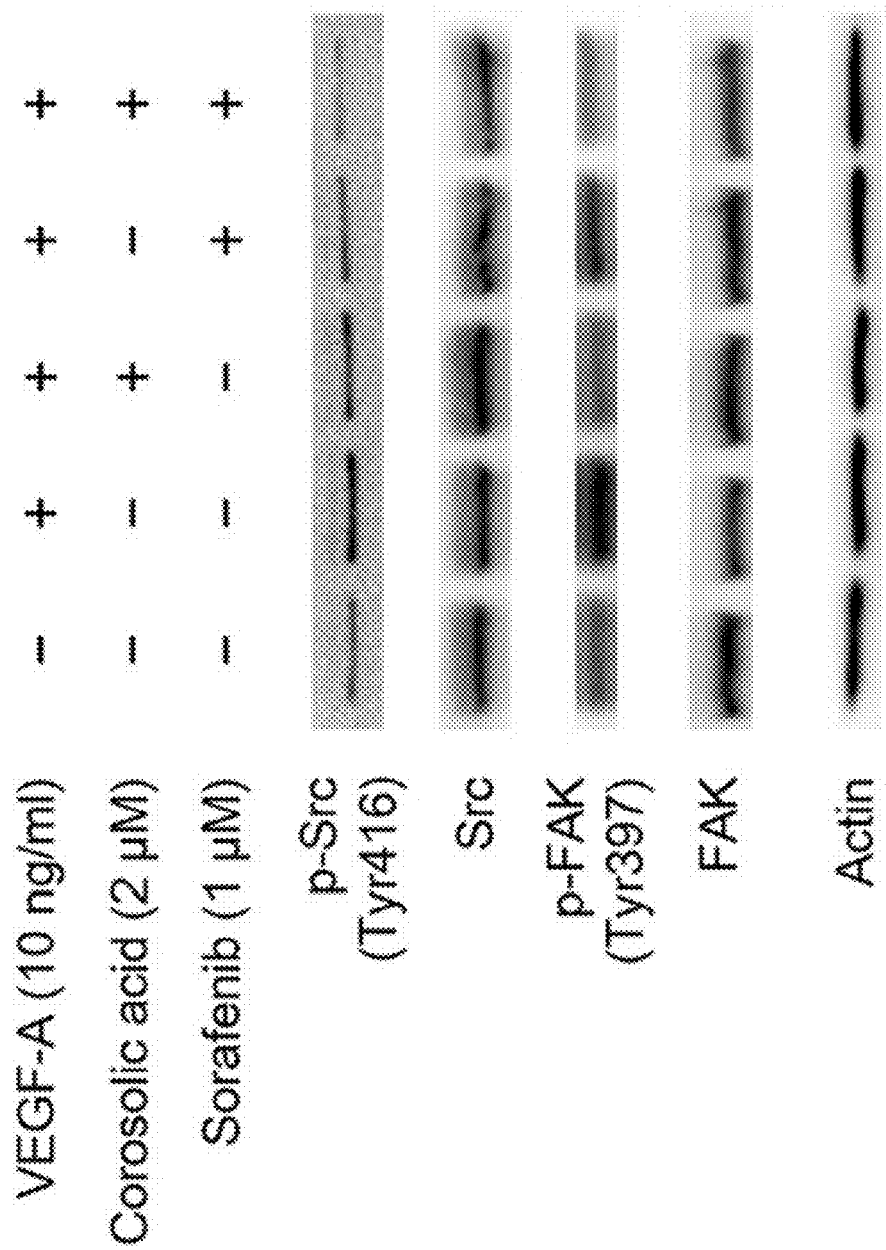

PHARMACEUTICAL COMPOSITION AND USE THEREOF

BACKGROUND OF THE INVENTION

1. Field of the Invention

The present invention relates to pharmaceutical compositions and uses thereof, and more particularly, to a pharmaceutical composition for treating hepatocellular carcinoma and use thereof.

2. Description of Associated Art

Hepatocellular carcinoma (HCC) is the fifth most commonly occurring cancer and the third most common cause of cancer-related deaths. Although the prognosis of HCC is poor, surgical resection and liver transplantation often have curative effects in patients.

Cancer cell migration is a critical process in tumor development and metastasis, and thus, anti-migration therapy is considered to be one of the approaches for cancer treatment. VEGF receptor signaling, such as VEGFR2 (KDR) signaling, has been implicated in HCC migration. The activation of downstream kinase, such as Src, FAK, and Rho-GTPase, induced by phosphorylated VEGFR2 results in remodeling of actin filaments and induction of migratory activity of tumor cells [1-4]. Previous studies have shown that knockdown of VEGFR suppresses HCC cell migration. The inhibition of VEGFR2 has been proposed as a novel therapeutic strategy for HCC patients. Various VEGFR2 kinase inhibitors such as sorafenib, sunitinib, and linifanib were developed and used in clinical trials.

Previous studies have discussed the pharmacophore modeling of different VEGFR2 inhibitors [5]. These inhibitors could be divided in two types, sunitinib-like or sorafenib-like, depending on the interacting hydrogen bonds. Sunitinib-like inhibitors form hydrogen bonds with residues of Asp1044, Cys917, and Asn921 near the protein surface. Sorafenib-like inhibitors interact with Asp1044, Cys917, and Glu883.

Recently, anti-HCC therapy with sorafenib has been approved by FDA [6, 7]. Sorafenib is a tyrosine kinase inhibitor and the mechanism thereof is to inhibit the activity of Raf protein in cell, and then to block RAF/MEK/ERK signaling pathway and to inhibit kinases of cell surface, which results in cell death and inhibits angiogenesis. However, there still exists some common side effects of the sorafenib formulation as chemotherapy, for example hand-foot syndrome, skin rash, hair loss, itching, redness, hypophosphatemia, weight loss, diarrhea, abdominal pain, nausea, vomiting, gastrointestinal bleeding, anemia, lymphocyte count decreased, thrombocytopenia, neutropenia, sensory neuropathy, tiredness, difficulty with breathing, pulmonary hemorrhage, pain and so on.

As known from the above, the therapies for HCC are quite limited. The conventional anticancer medicaments may affect the other functions of the subjects. Therefore, an efficient therapy for inhibiting HCC with decreased side effects which affect normal function is urged.

SUMMARY OF THE INVENTION

In view of the above-described issues, the present invention provides a pharmaceutical composition comprising a therapeutically amount of compound represented by formula (1):

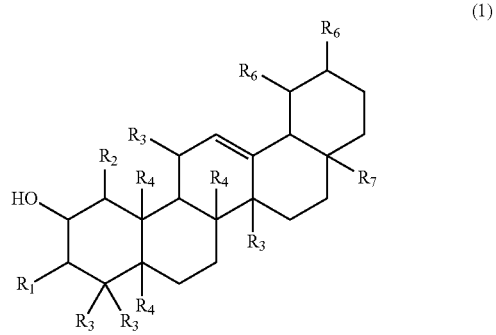

wherein $R_1$ is H, hydroxy or methyl;
$R_2$ is H, $C_1$-$C_3$alkyl, hydroxy, —CN or halogen;
each of $R_3$ and $R_4$ is independently selected from the group consisting of H, $C_1$-$C_3$alkyl, hydroxy, —CN, and halogen;
$R_5$ is H, hydroxy or methyl;
$R_6$ is H, $C_1$-$C_3$alkyl, hydroxy, —CN, halogen, or —COOR$_{11}$; and
$R_7$ is $C_1$-$C_3$alkyl or —COOR$_{11}$, wherein $R_{11}$ is H or $C_1$-$C_3$alkyl;
at least an anticancer agent, wherein the molar ratio of the compound and the at least an anticancer agent in the pharmaceutical composition is from 2:1 to 1:32; and
a pharmaceutically acceptable carrier.

In one embodiment, the compound represented by formula (1) is a compound represented by formula (2) (also referred to corosolic acid (CA) hereinafter):

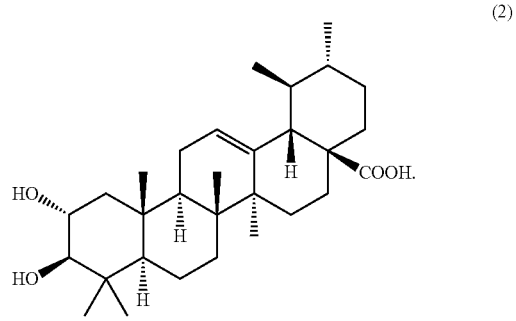

In one embodiment, the pharmaceutical composition of the present invention further comprises at least an anticancer agent in a therapeutically efficient amount, and the anticancer agent is multikinase inhibitor.

In one embodiment, the concentration of the compound represented by formula (1) is from 1 µM to 50 µM and the concentration of the at least an anticancer agent is from 1 µM to 10 µM. In one embodiment, the molar ratio of the compound represented by formula (1) and the at least an anticancer agent in the pharmaceutical composition is from 2:1 to 1:32.

The present invention further provides a use of a compound represented by formula (1) for the manufacture of a medicament for treating hepatocellular carcinoma and/or inhibiting proliferation or migration of hepatocellular carcinoma cells. In one embodiment, the medicament inhibits VEGFR2 kinase, VEGFR2/Src/FAK/cdc42 pathway and actin remodeling.

In one embodiment, the therapeutically efficient amount of the medicament administrated to a subject is from 2.5 mg to 5 mg of the compound per kilogram of body weight.

In another embodiment, the therapeutically efficient amount of the medicament administrated to a subject such as human is from 0.2 mg to 0.42 mg of the compound per kilogram of body weight.

In one embodiment, the medicament comprises at least an anticancer agent, wherein the medicament administered to a subject is from 12.5 mg to 25 mg per kilogram of bodyweight, and the therapeutically efficient amount of the at least an anticancer agent is from 10 mg to 20 mg per kilogram of bodyweight.

The present invention further provides a use of a compound represented by formula (2) for the manufacture of a medicament for treating hepatocellular carcinoma and/or inhibiting proliferation or migration of hepatocellular carcinoma cells,

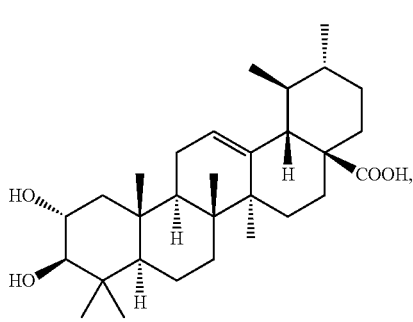

(2)

wherein, the medicament further comprises at least an anticancer agent, and the molar ratio of the compound represented by formula (2) and the at least an anticancer agent is from 2:1 to 1:32 in the medicament.

The pharmaceutical composition provided by the present invention can treat HCC efficiently and can inhibit the kinase activity in HCC cells and the actin activity therein, and thereby to inhibit proliferation and migration of HCC cells.

BRIEF DESCRIPTIONS OF THE DRAWINGS

FIG. 1A illustrates the cytotoxicity of CA on Huh7 cell lines; FIG. 1B illustrates the cytotoxicity of CA on HepG2 cell lines; and FIG. 1C illustrates the cytotoxicity of CA on Hep3B cell lines. Results are presented as mean values±SE. ( indicates P<0.01 and * indicates P<0.001 as compared with the control group).

FIG. 2A illustrates that the inhibition of migration activity of Huh7 cell lines caused by CA is in a dose-dependent manner; FIGS. 2B and 2C respectively illustrate that the migration activities of HepG2 and Hep3B cell lines were inhibited by CA in a dose-dependent manner; and FIG. 2D illustrates the effects of CA, sorafenib and ursolic acid on the migration activity of Huh7cell lines. Results are presented as mean values±SE. ( indicates P<0.01 and * indicates P<0.001 as compared with the control group).

Figure 8A:
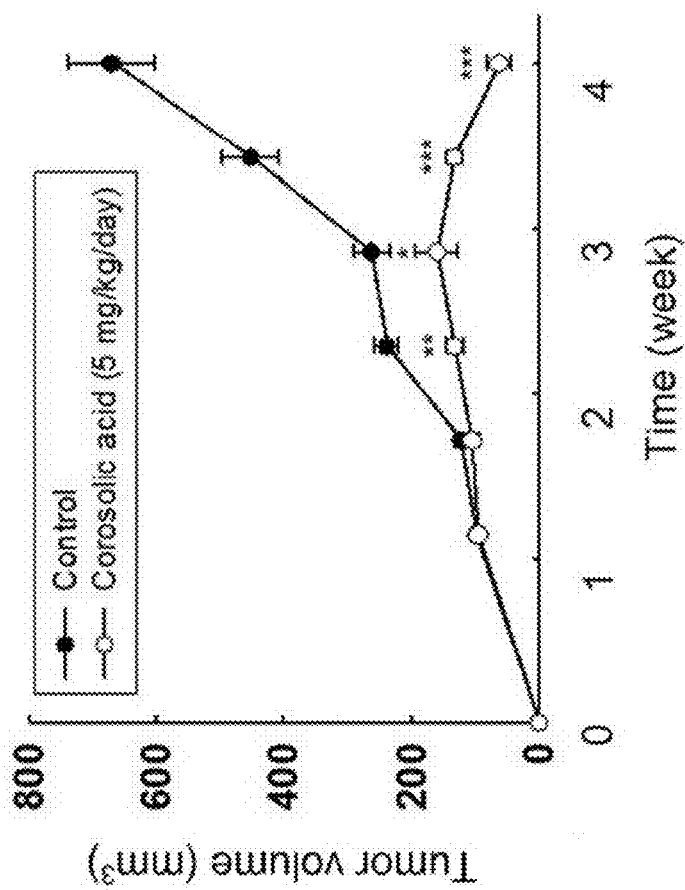
Figure 8A:
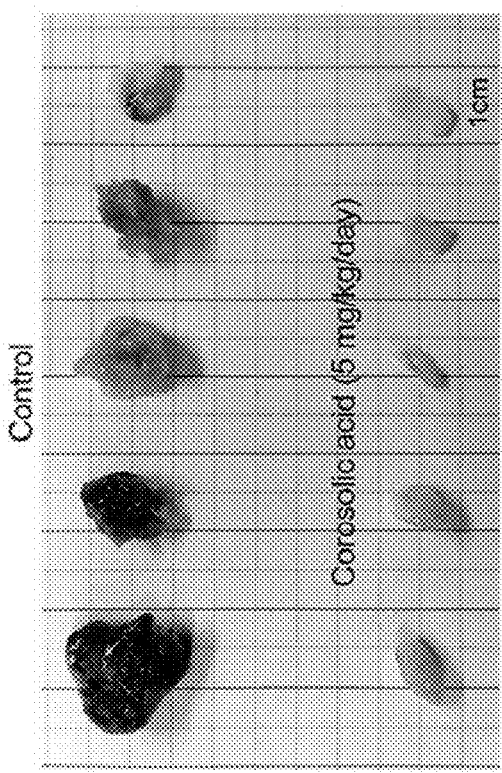
Figure 8B:
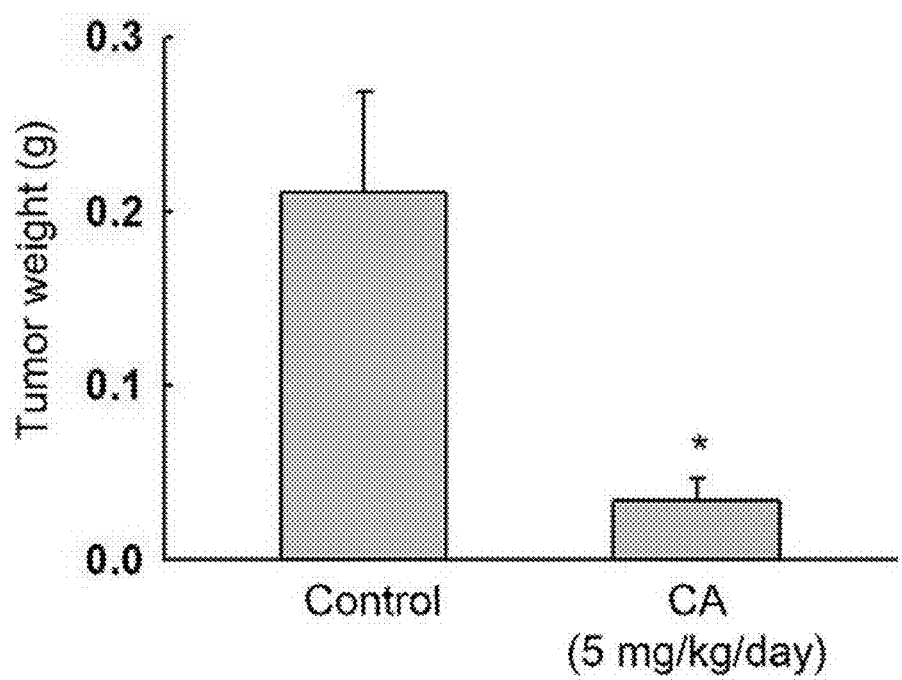
Figure 8C:
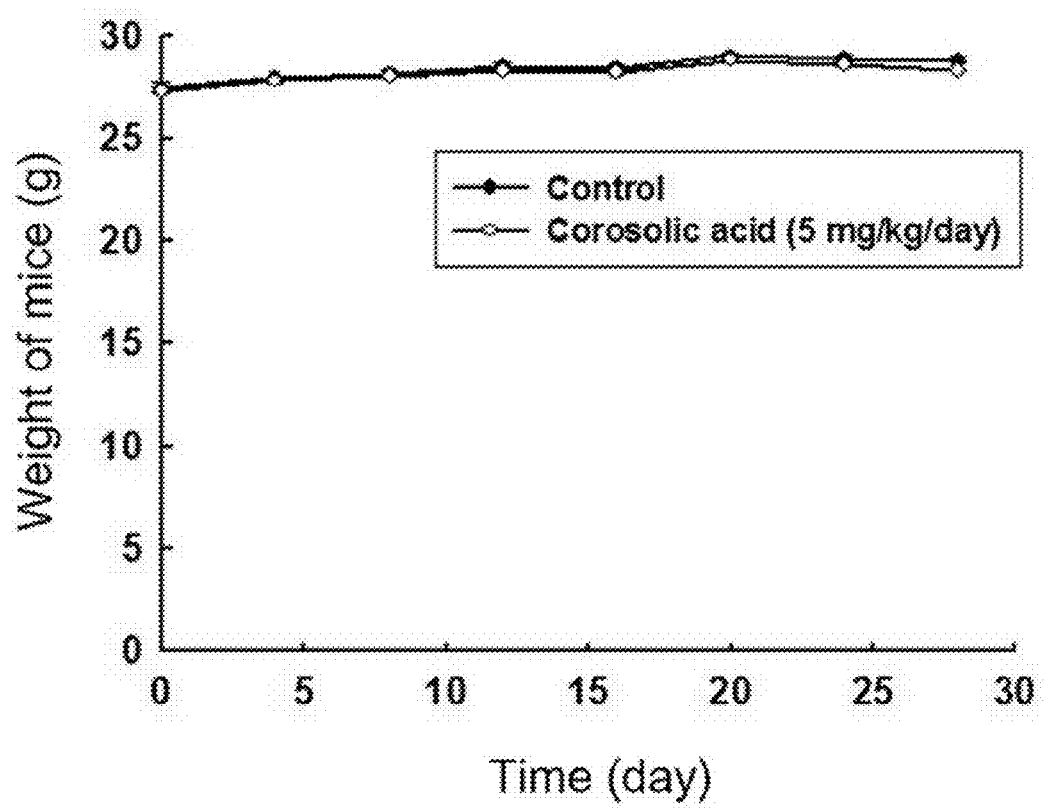

FIGS. 8A to 8C illustrate the antitumor effect of CA on Huh7 cell lines in mice. FIG. 8A illustrates representative appearances of excised tumors and tumor volume at different time points; FIG. 8B illustrates weights of tumor mass; and FIG. 8C illustrates bodyweight between mice treated with and without CA.

Figure 9:
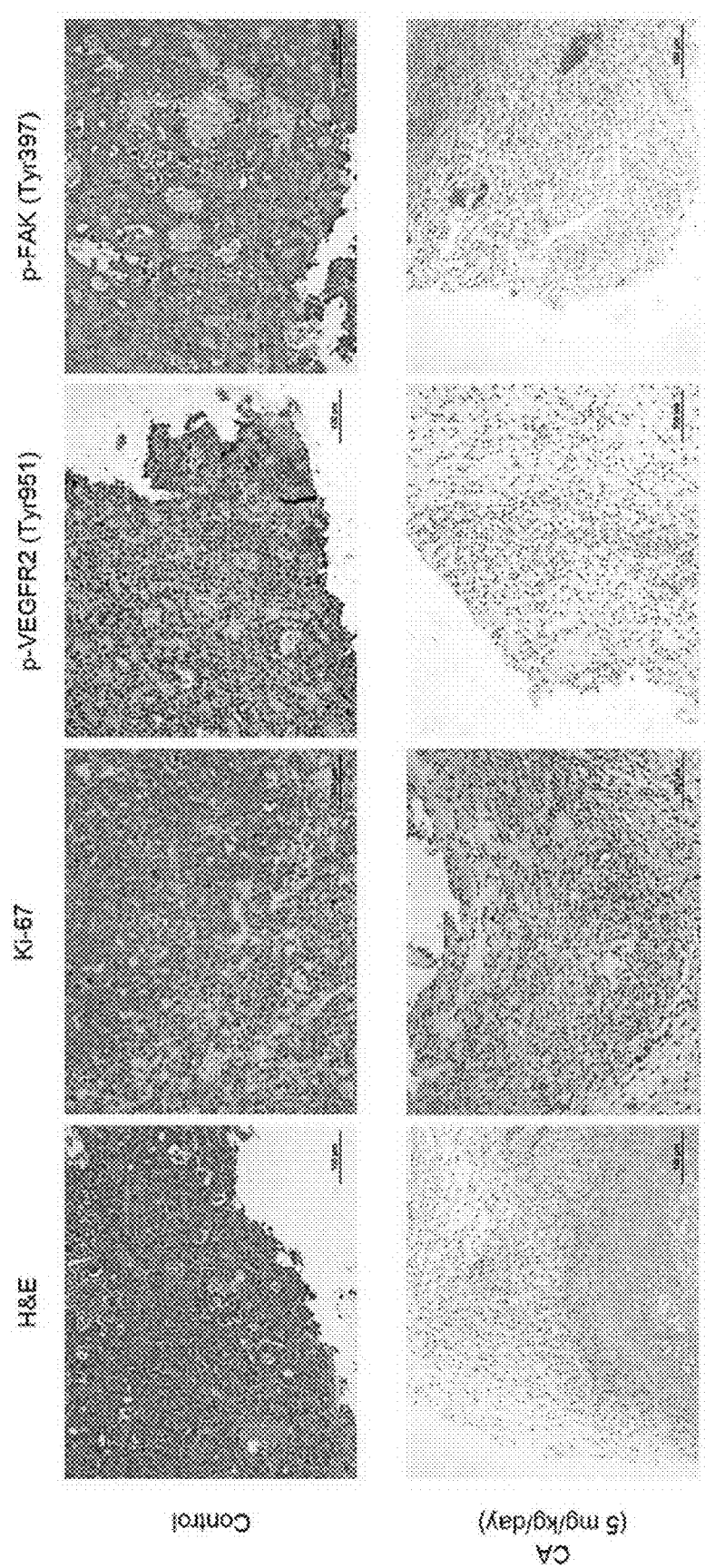

FIG. 9 shows immunostaining of Ki-67, p-VEGFR2 (Tyr951) and p-FAK (Tyr397) in excised tumor in mice.

Figure 10A:
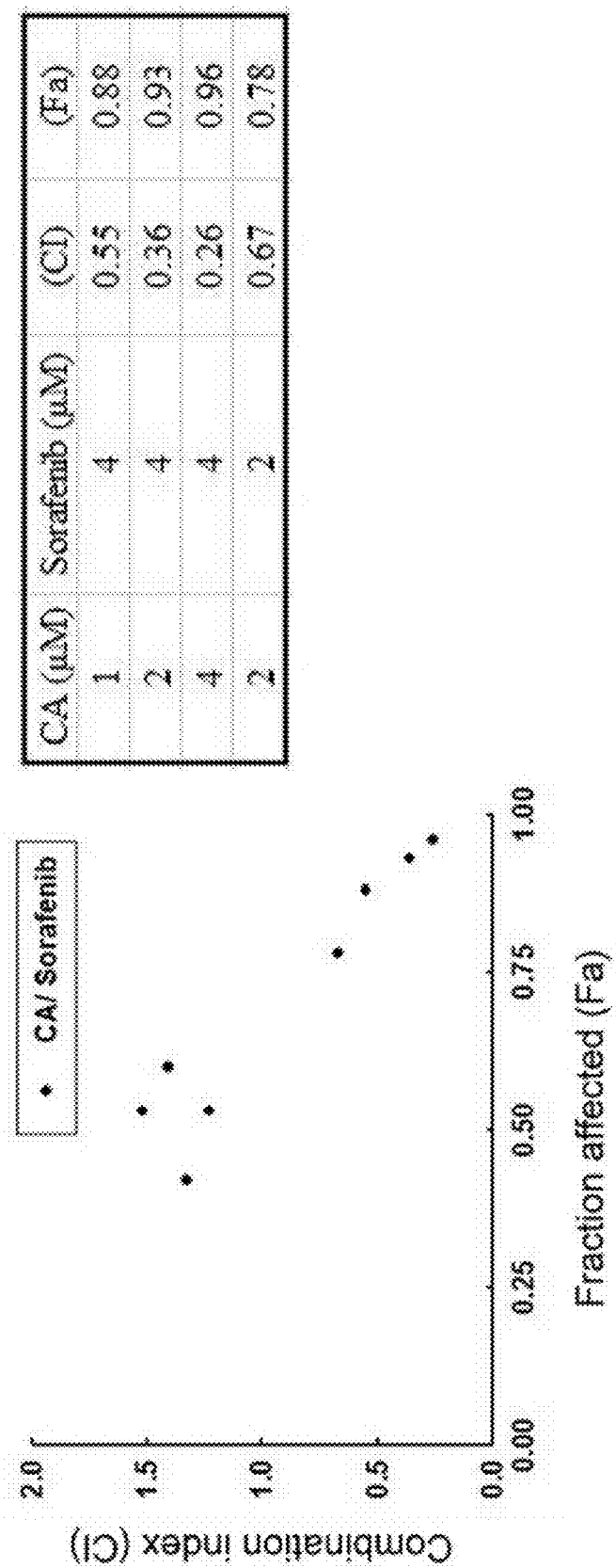
Figure 10C:
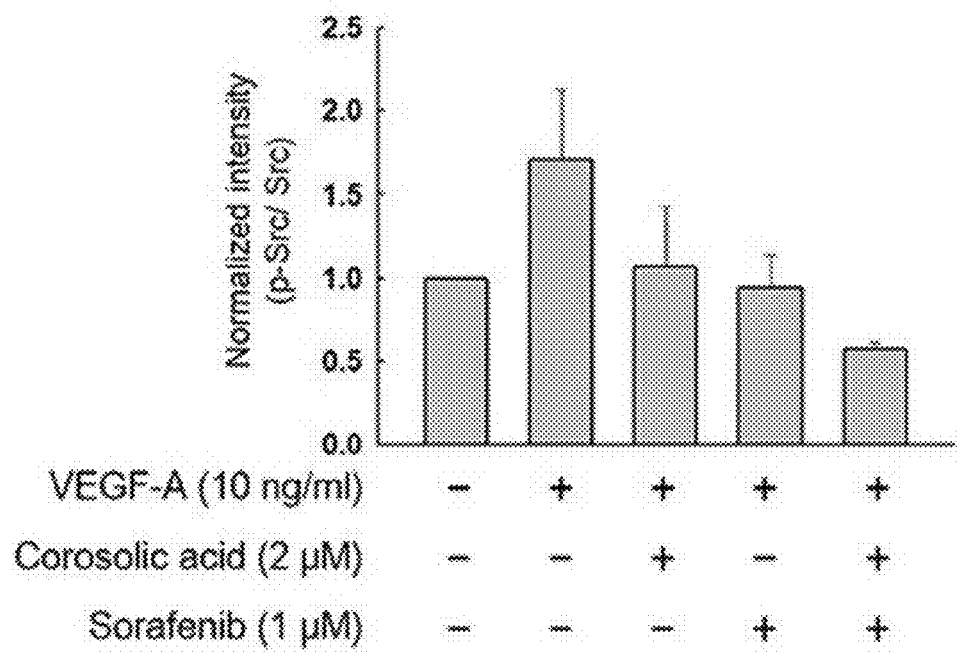
Figure 10D:
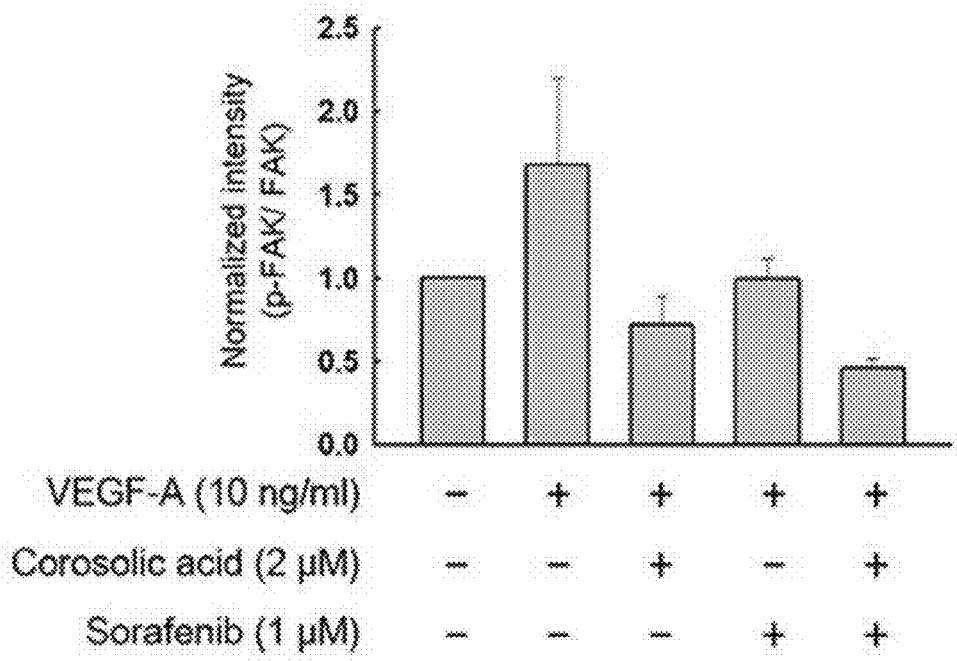
Figure 10E:
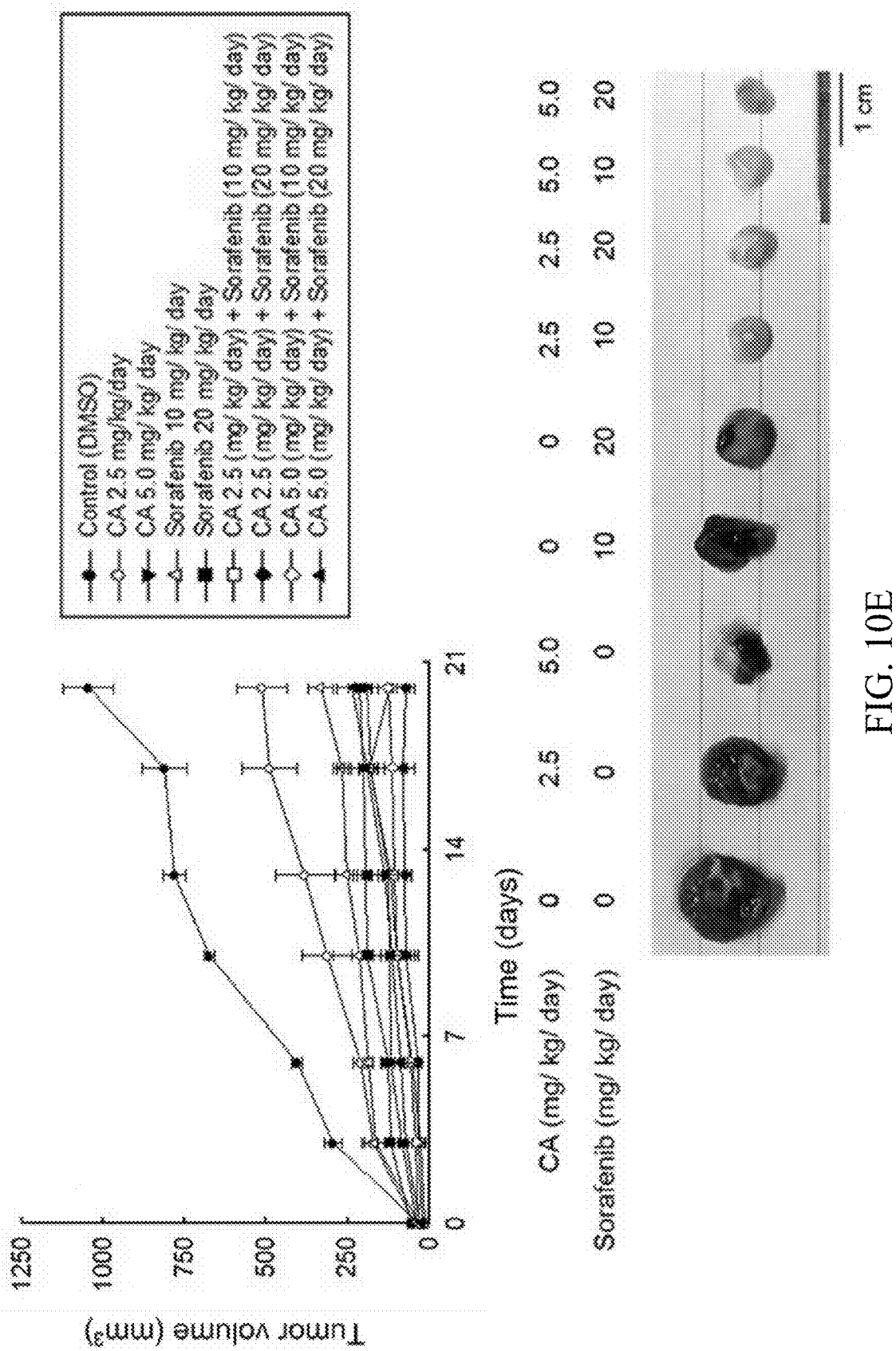
Figure 10F:
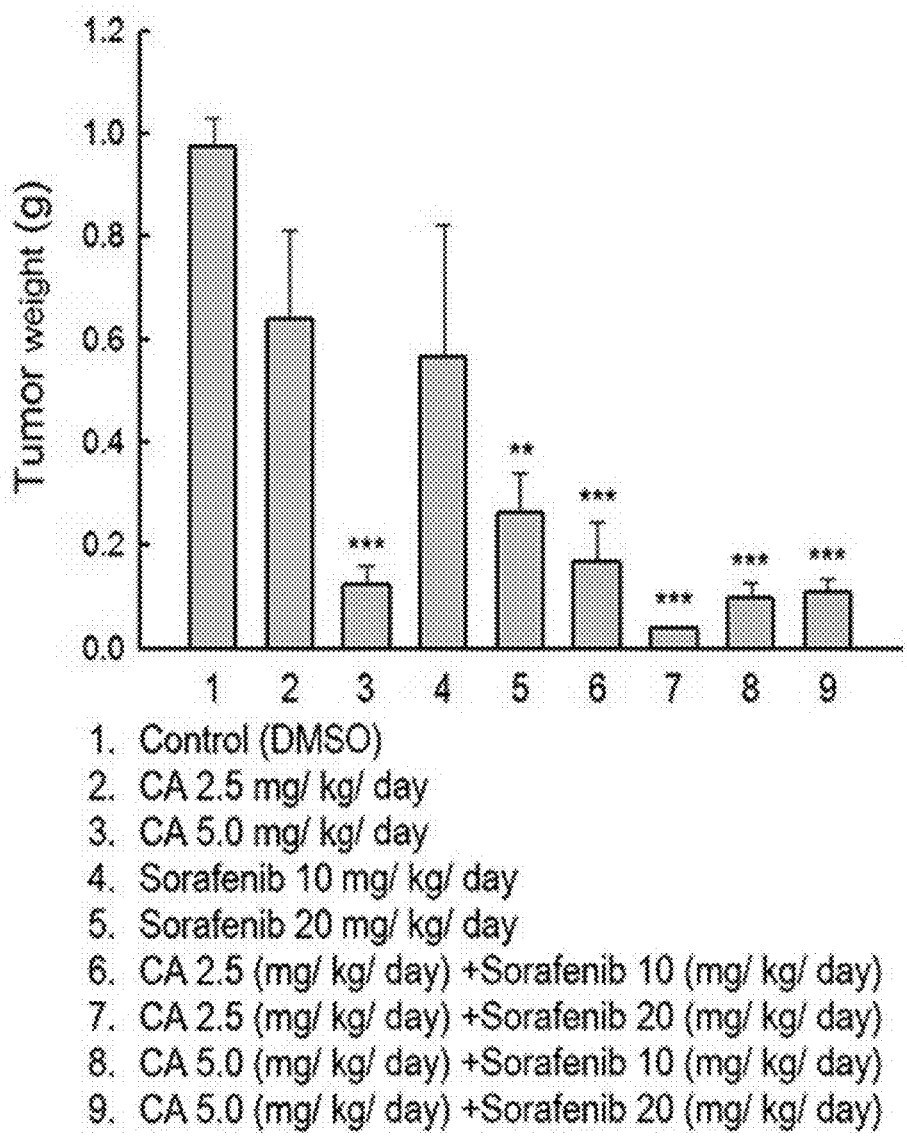
Figure 10G:
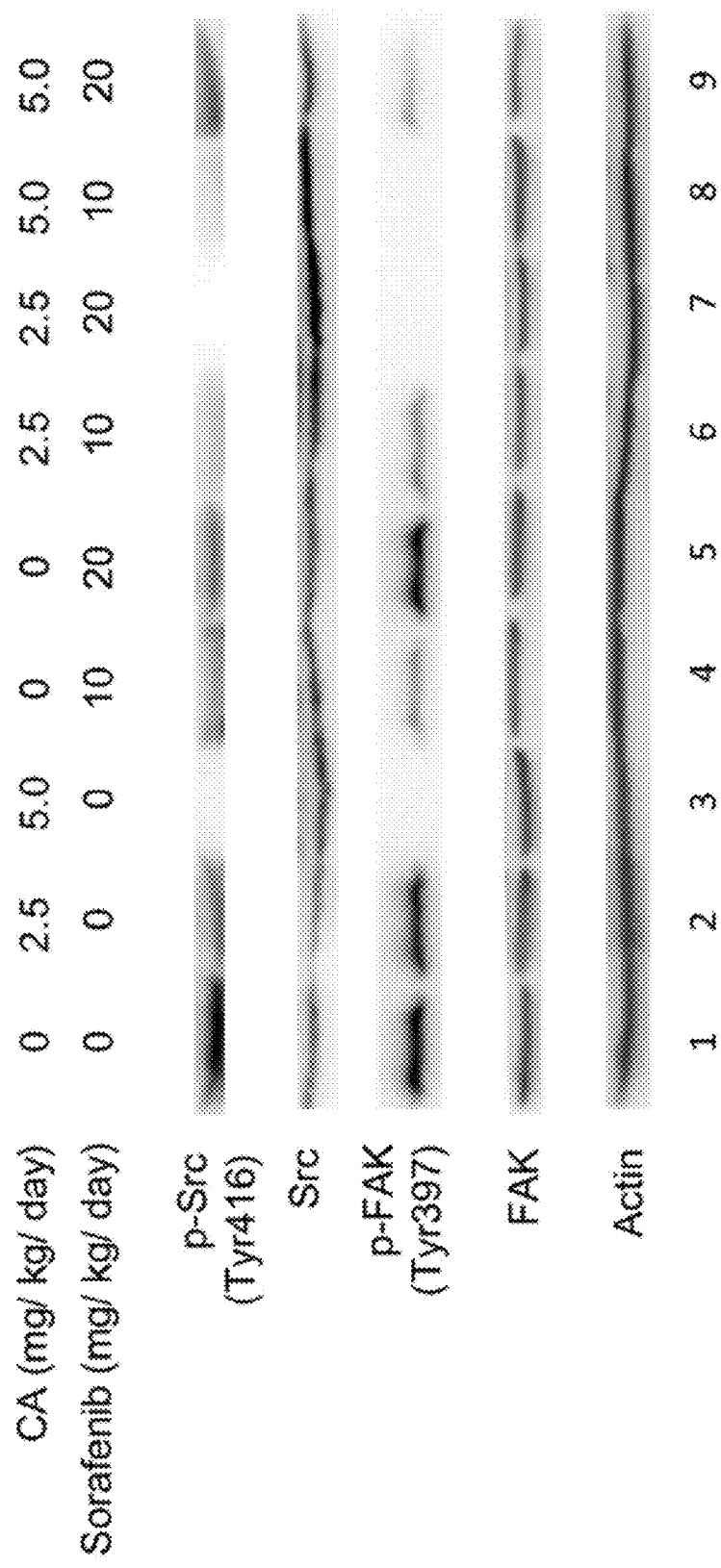
Figure 10H:
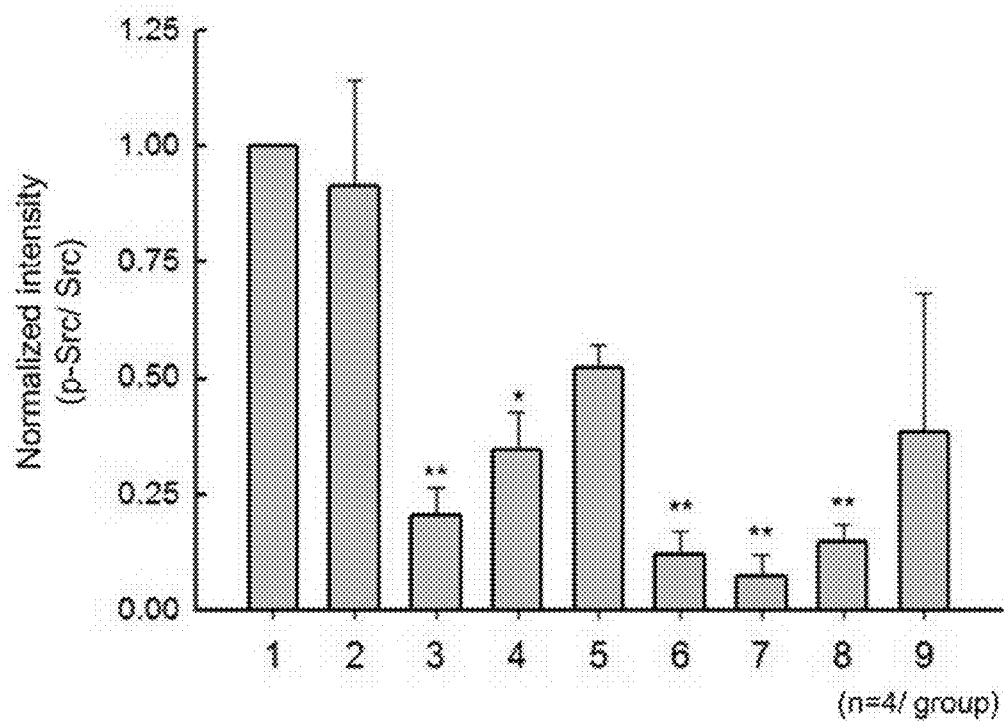
Figure 10I:
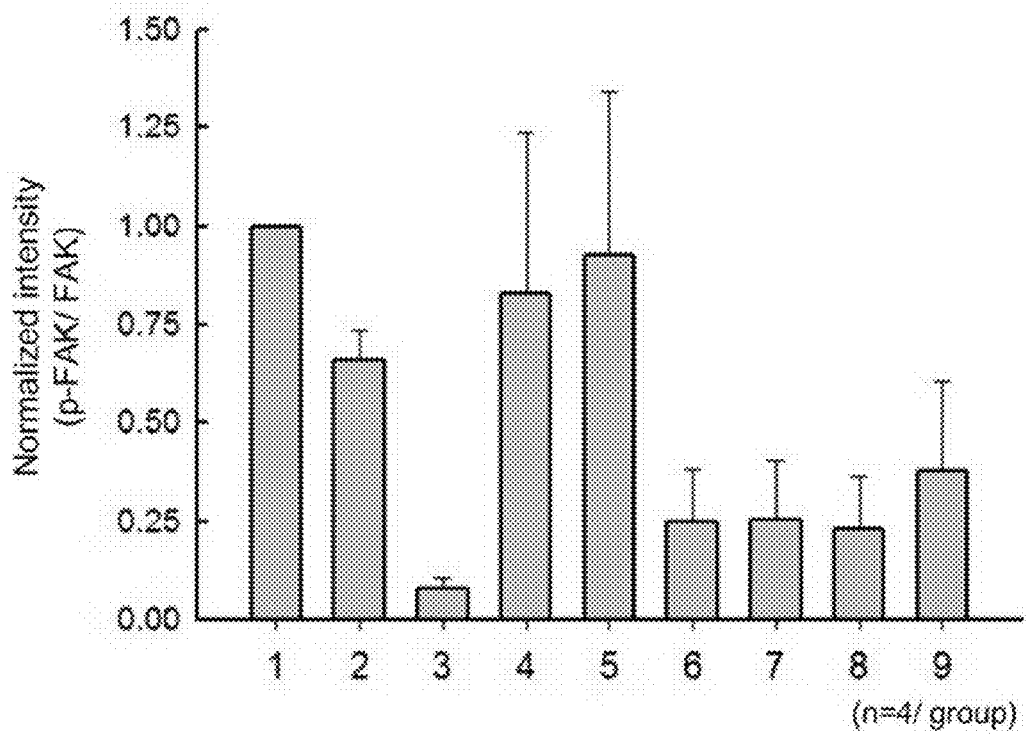

FIG. 10A illustrates combination effects of CA and sorafenib on the inhibitory migration of Huh7 cell lines. The combination index (CI) values were examined at different levels of migration inhibition effect (fa); FIGS. 10B to 10D illustrate the results of the phosphorylation level and the normalized intensity of Src and FAK of Huh7 cell lines treated with different compounds and analyzed by Western blot; FIG. 10E illustrates the effect of combination of CA and sorafenib on the tumor growth in mice; FIG. 10F illustrates effect of combination of CA and sorafenib on the weight of tumor mass in mice and the CI value thereof; and FIGS. 10G to 10I illustrate that combination of CA and sorafenib inhibit Src and FAK kinase in vivo.

Figure 11A:
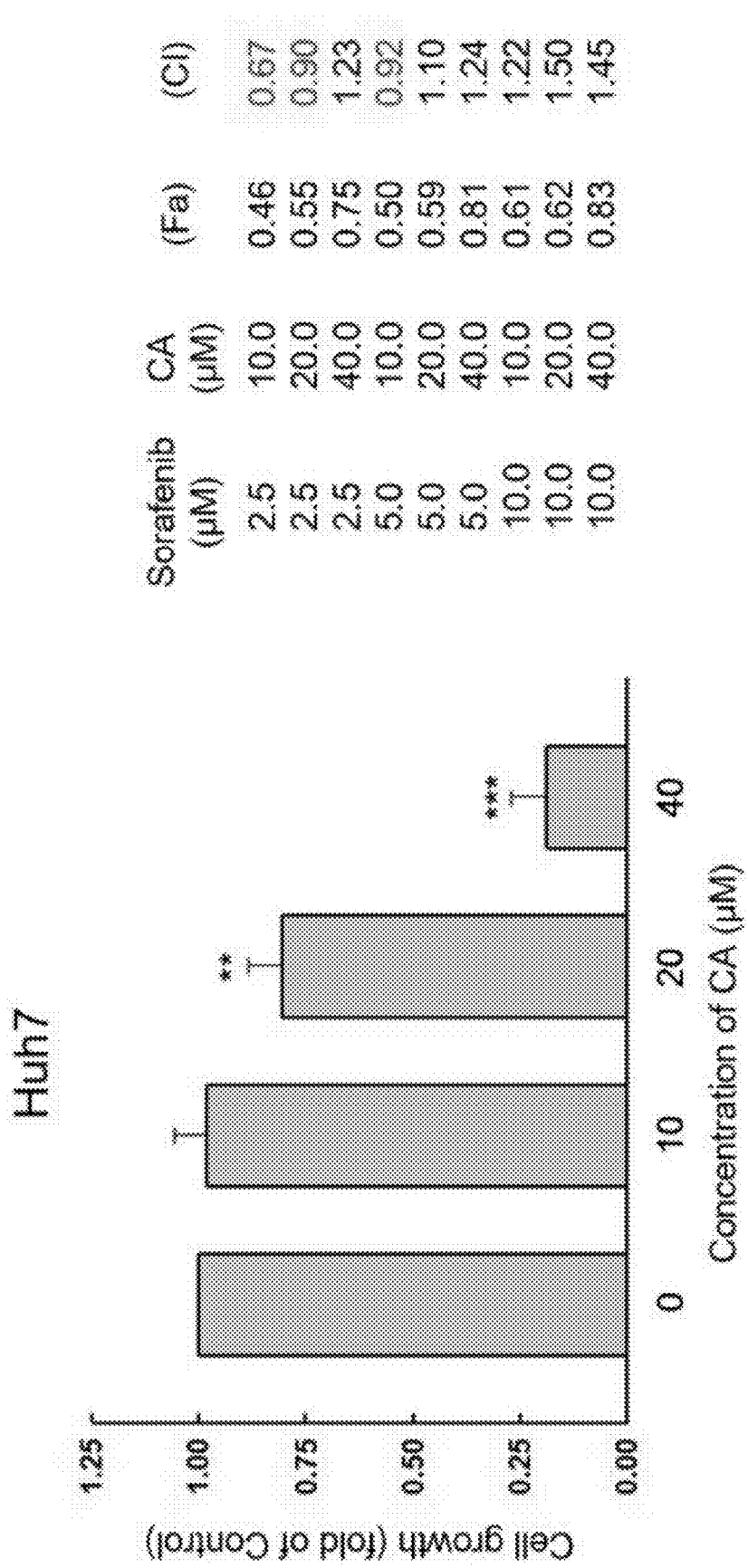
Figure 11B:
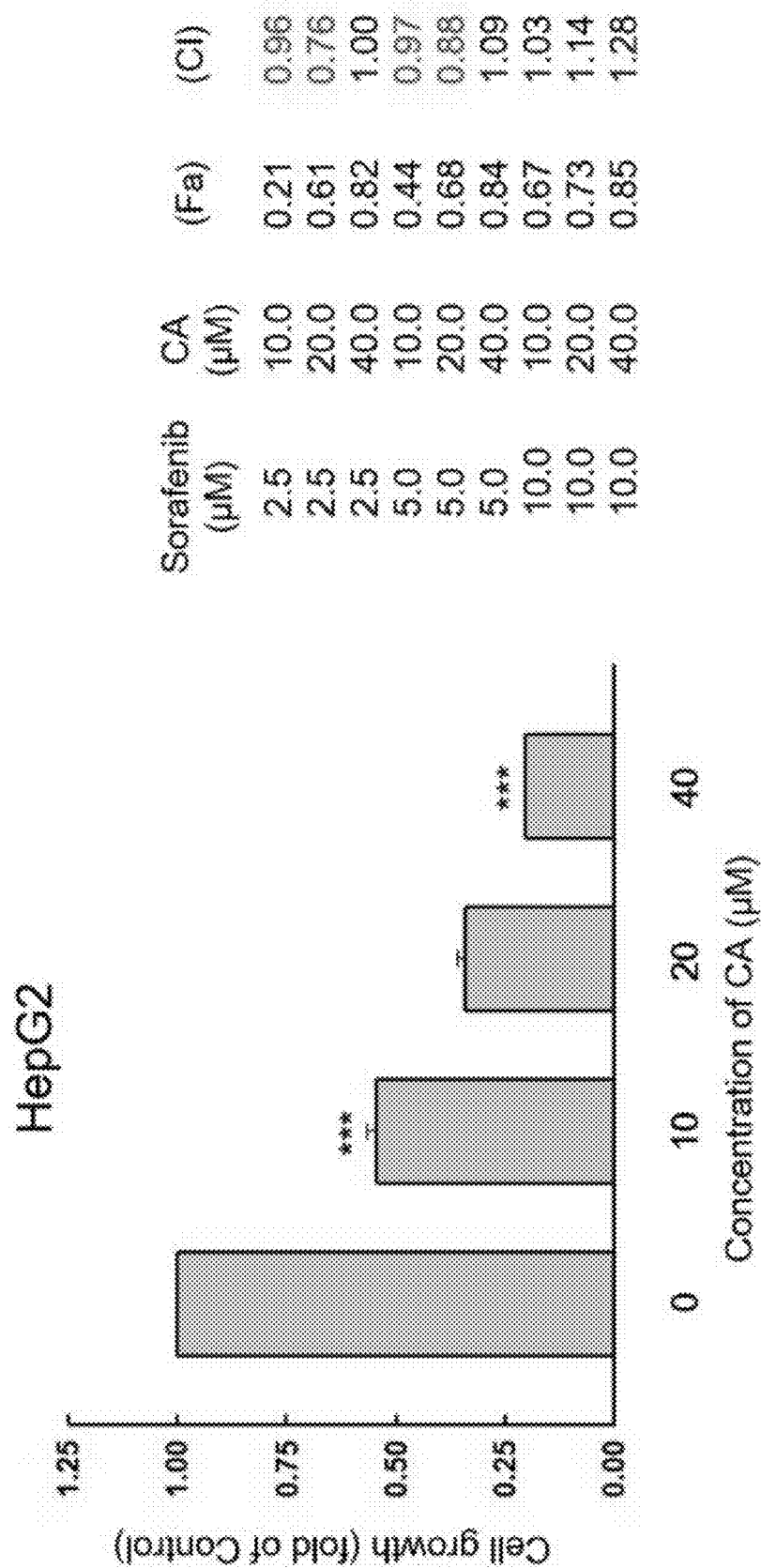
Figure 11C:
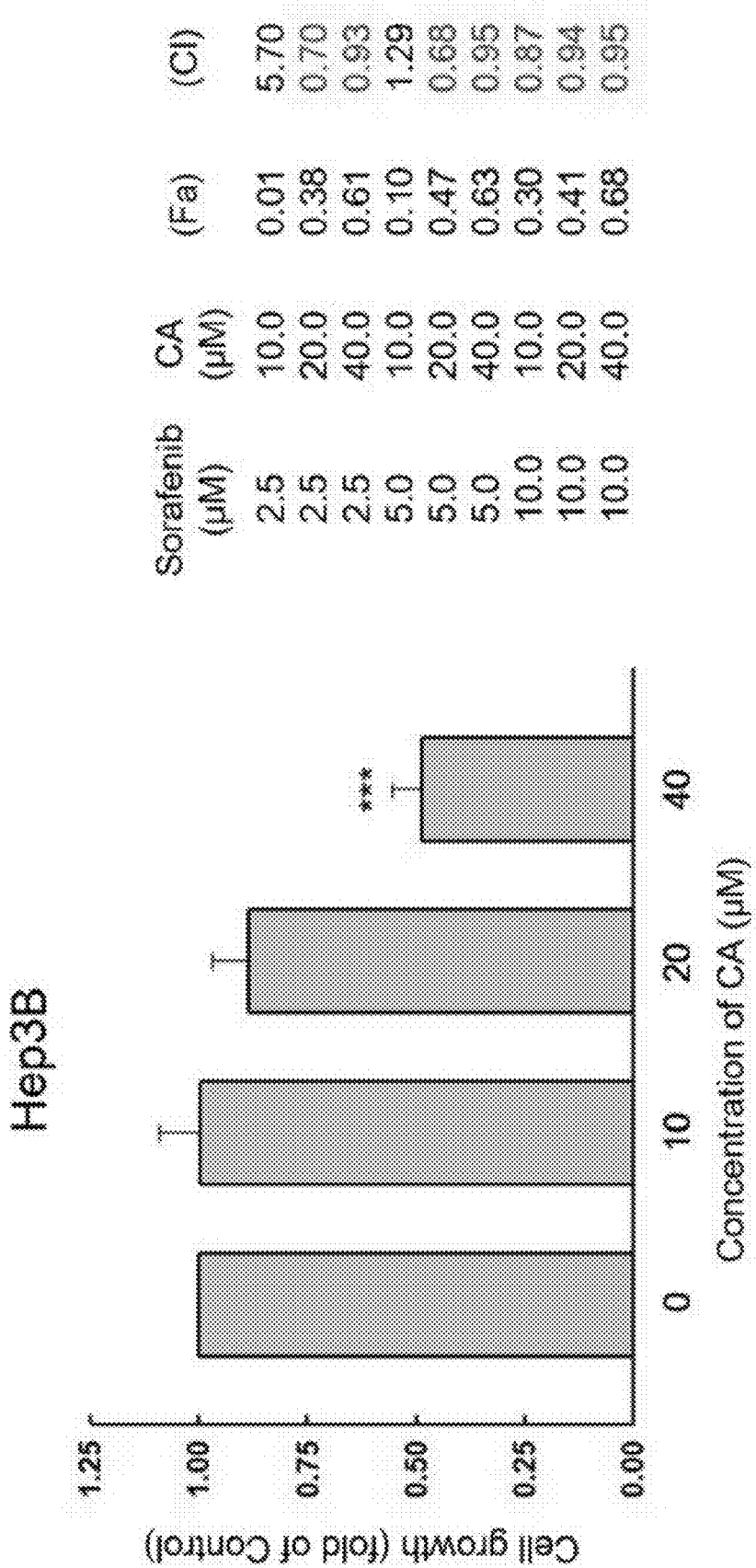

FIGS. 11A to 11C respectively illustrate the combination of CA and sorafenib inhibits the growth of Huh7, HepG2 and H3p3B cell lines.

Figure 12A:
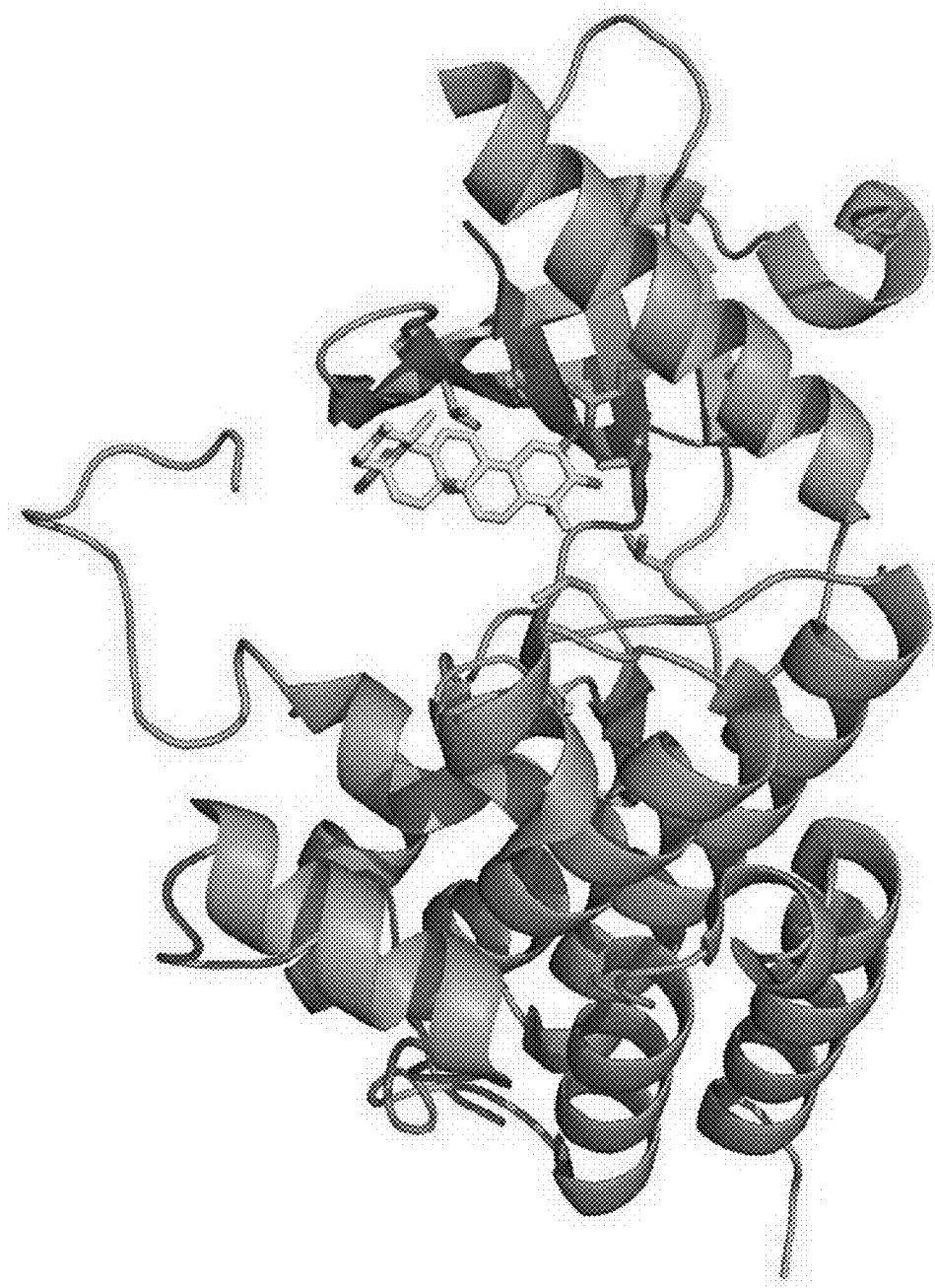
Figure 12B:
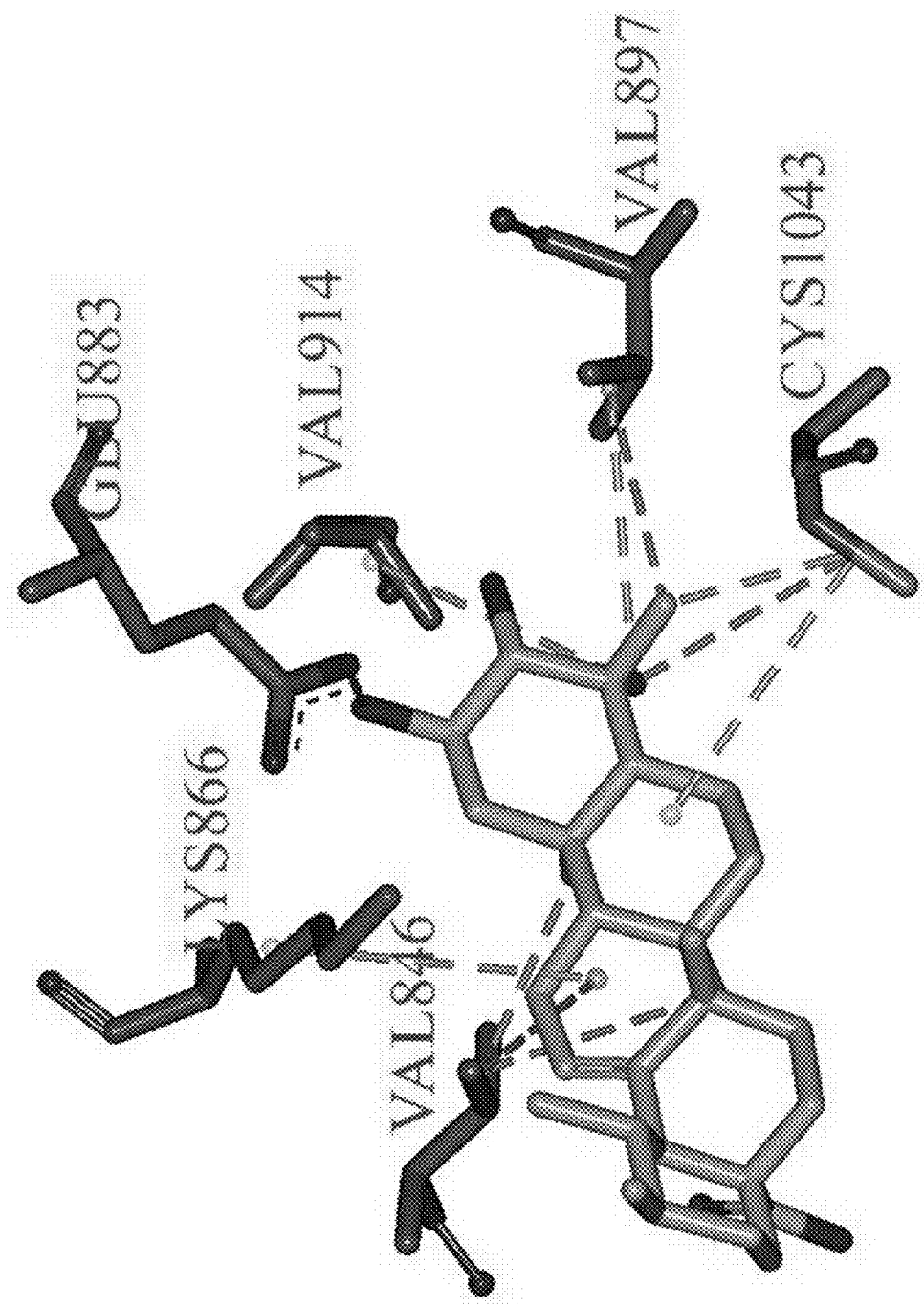

FIGS. 12A and 12B illustrate the interaction of CA to the ATP binding site of VEGFR2 (PDB code: 1YWN); FIG. 12A shows the three-dimensional diagram of the interaction of CA to the ATP binding site of VEGFR2; and FIG. 12B shows the interaction of CA with the main amino acid residues in the ATP-binding site of VEGFR2.

DETAILED DESCRIPTION OF THE PREFERRED EMBODIMENTS

The present invention is described by using the following embodiments, so as to enable a person skilled in the art to conceive the other advantages and effects of the present invention from the invention of the present specification. However, the examples in the present invention are not used for limiting the scope of the present application. Any one skilled in the art can alter or modify the present invention in any way, without departing from the spirit and scope thereof. Therefore, the scope of the present invention should be accorded with the definitions in the appended claims.

The present invention provides a pharmaceutical composition, comprising a therapeutically efficient amount of compound represented by formula (1):

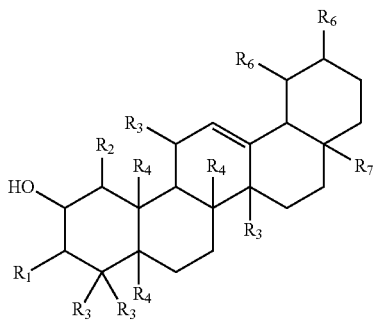

(1)

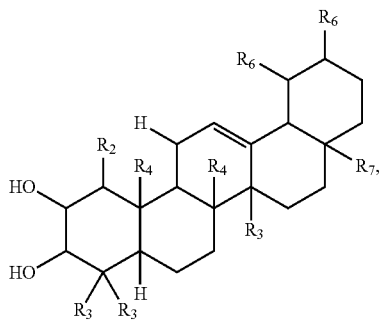

(1-2)

wherein $R_1$ can be H, hydroxy or methyl;

$R_2$ can be H, $C_1$-$C_3$alkyl, hydroxy, —CN or halogen;

each of $R_3$ and $R_4$ can respectively be H, $C_1$-$C_3$alkyl, hydroxy, —CN or halogen;

$R_5$ can be H, hydroxy or methyl;

$R_6$ can be H, $C_1$-$C_3$alkyl, hydroxy, —CN, halogen, or —COOR$_{11}$; and $R_7$ can be $C_1$-$C_3$alkyl or —COOR$_{11}$, wherein $R_{11}$ can be H or $C_1$-$C_3$alkyl;

at least an anticancer agent, wherein the molar ratio of the compound and the at least an anticancer agent in the pharmaceutical composition can be from 2:1 to 1:32; and at least one pharmaceutically acceptable carrier.

The compound represented by formula (1) can be a compound represented by formula (1-1):

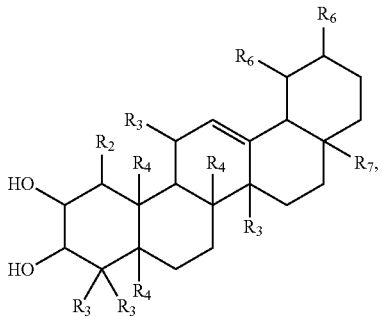

(1-1)

wherein $R_2$ can be H, $C_1$-$C_3$alkyl, hydroxy, —CN or halogen;

each of $R_3$ and $R_4$ can respectively be H, $C_1$-$C_3$alkyl, hydroxy, —CN or halogen;

$R_5$ can be H, hydroxy or methyl;

$R_6$ can be H, $C_1$-$C_3$alkyl, hydroxy, —CN, halogen, or —COOR$_{11}$; and $R_7$ can be $C_1$-$C_3$alkyl or —COOR$_{11}$, wherein $R_{11}$ can be H or $C_1$-$C_3$alkyl.

The compound represented by formula (1) can be a compound represented by formula (1-2):

wherein $R_2$ can be H, $C_1$-$C_3$alkyl, hydroxy, —CN or halogen;

each of $R_3$ and $R_4$ can respectively be H, methyl, hydroxy or —CN;

$R_5$ can be hydroxy or methyl;

$R_6$ can be $C_1$-$C_3$alkyl, hydroxy, —CN, halogen, or —COOR$_{11}$; and $R_7$ can be $C_1$-$C_3$alkyl or —COOR$_{11}$, wherein $R_{11}$ can be H or $C_1$-$C_3$alkyl.

Preferably, in one embodiment of the compound represented by formula (1), $R_1$ is hydroxy and each of $R_3$ and $R_4$ is independently selected from the group consisting of methyl, ethyl, and —CN.

More preferably, the compound represented by formula (1) can be the compound represented by formula (2):

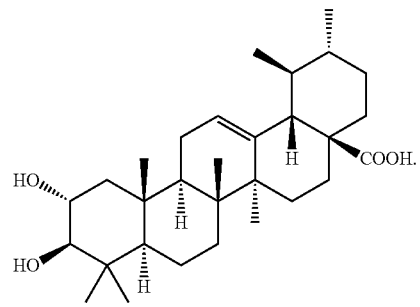

(2)

The pharmaceutical composition provided by the present invention can comprise at least an anticancer agent in a therapeutically efficient amount.

According to one embodiment of the present invention, the anticancer agent can preferably be a kinase inhibitor, for example, cetuximab, trastuzumab, rituximab, brivanib, cediranib, gefitinib, erlotinib, foretinib, lapatinib, linifanib, imatinib, pazopanib, ramucirumab, sorafenib, sunitinib, TSU-68, vandetanib, vatalanib, bortezomib, temsirolimus, bevacizumab, thalidomide, etc.

According to one embodiment of the present invention, the anticancer agent can be more preferably a multikinase inhibitor, for example, sorafenib, brivanib, bevacizumab, linifanib, pazopanib, vatalanib, cediranib, ramucirumab, TSU-68, vandetanib, foretinib, sunitinib, etc.

According to one embodiment of the present invention, the multikinase inhibitor can be sorafenib.

According to one embodiment of the present invention, the concentration of the compound represented by formula (1) can be from 1 μM to 50 μM, and the concentration of the at least an anticancer agent can be from 1 μM to 10 μM.

According to one embodiment of the present invention, the molar ratio of the compound represented by formula (1) and the anticancer agent in the pharmaceutical composition can be from 2:1 to 1:32. Preferably, the molar ration of the compound represented by formula (1) and the anticancer agent in the pharmaceutical composition can be from 1:2 to 1:16.

The present invention also provides a use for the manufacture of a medicament for treating hepatocellular carcinoma and/or inhibiting proliferation or migration of hepatocellular carcinoma cells, and the medicament comprises the compound represented by formula (1). The medicament can inhibit VEGFR2 kinase, VEGFR2/Src/FAK/cdc42 pathway and actin remodeling.

In one embodiment of the use for the manufacture of a medicament for treating hepatocellular carcinoma and/or inhibiting proliferation or migration of hepatocellular carcinoma cells, $R_1$ of the compound represented by formula (1) can be hydroxy; and $R_3$ and $R_4$ can be independently selected from methyl, ethyl or —CN.

According to another embodiment of the use for the manufacture of a medicament for treating hepatocellular carcinoma and/or inhibiting proliferation or migration of hepatocellular carcinoma cells of the present invention, the compound is represented by formula (2) and the medicament can comprise at least one anticancer agent

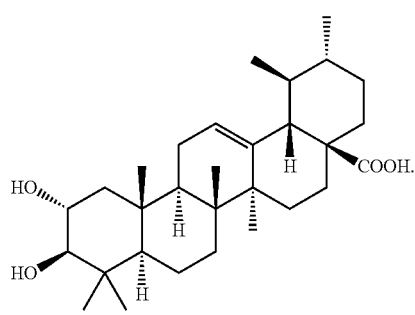

(2)

According to the present invention, a therapeutically efficient amount of the medicament administrated to a subject can be varied according to the well-known dosage adjustment condition, such as the personal conditions (including species, gender, ages), the severity of the disease, other diseases or disorders, and therapies given for other diseases.

The subject can be, for example but not limited to, mice, rats, hamsters, guinea pigs, mink, rabbits, dogs, primates, pigs, bovines, sheep, goats, etc. When the species administrated are varied, the efficient amount of the medicament of the present invention can be adjusted as needed. The adjustment method can be any method known in the art, for example, the conversion of Animal Doses to Human Equivalent Doses disclosed by the Guidance for Industry: Estimating the Maximum Safe Starting Dose in Initial Clinical Trials for Therapeutics in Adult Healthy Volunteers (2005) published by FDA can be used, which is incorporated herein by reference.

According to one embodiment of the present invention, the therapeutically efficient amount of the medicament administered to a subject can be 2.5 mg to 5 mg of the compound per kilogram of bodyweight. According to this embodiment, the subject can be a mammal. Preferably, the subject can be a mouse.

According to another embodiment of the present invention, the therapeutically efficient amount of the medicament administrated to a subject can be 0.2 mg to 0.42 mg of the compound per kilogram of bodyweight. According to this embodiment, the subject can be a mammal. Preferably, the subject can be a human.

According to one embodiment of the present invention, the medicament can further comprises at least one anticancer agent, wherein the therapeutically efficient amount of the medicament administrated to a subject can be from 12.5 mg to 25 mg per kilogram of bodyweight and the therapeutically efficient amount of the at least one anticancer agent can be 10 mg to 20 mg per kilogram of body weight.

According to one embodiment of the present invention, the at least one anticancer agent can be a multikinase inhibitor. Preferably, the multikinase inhibitor can be sorafenib.

According to one embodiment of the present invention, the molar ration of the compound and the at least one anticancer agent in the medicament can be from 2:1 to 1:32. For example, in the use of the compound represented by formula (2) for the manufacture of a medicament for treating hepatocellular carcinoma and/or inhibiting proliferation or migration of hepatocellular carcinoma cells, the molar ratio of the compound represented by formula (2) and the at least an anticancer agent in the medicament can be from 2:1 to 1:32.

Besides, according to one embodiment of the use of the compound represented by formula (2) for the manufacture of a medicament for treating hepatocellular carcinoma and/or inhibiting proliferation or migration hepatocellular carcinoma cells of the present invention, the at least one anticancer agent is multikinase inhibitor, for example, sorafenib.

The medicament of the present invention can be administrated by any means known in the art such as oral administration, parenteral administration, intravenous administration or by injection, for example, subcutaneous infection or intraperitoneal injection and the like.

The effects of the present disclosure are further illustrated by the following specific embodiments, which are not intended to limit the scope of the invention.

EXAMPLES

Example 1: Preparation of the Compound Represented by Formula (2)

The plant materials (*Actinidia chinensis*) were boiled in water and concentrated to 1 g/mL with an evaporator, and the stock solutions obtained were stored at −20° C. for the next step. Water extracts obtained from *A. chinensis* can also be commercially available (e.g., purchased from Sigma-Aldrich). The contents in the water extracts of *A. chinensis* were analyzed by high performance liquid chromatography-diode array/evaporative light scattering detector (HPLC-DAD/ELSD) under the following conditions: a linear gradient of ddH$_2$O to methanol for 60 mins, and followed by 100% methanol for another 10 mins at a flow rate of 1 mL/minute. The result shows that CA is about 8.4% of the dry weight of *A. chinensis*.

Example 2: Evaluation of Cytotoxicity of CA 2-1. Cell Culture

The HCC cell lines: Huh7, HepG2 and Hep3B were obtained from Japanese Collection of Research Bioresources (National Institute of Health Sciences; Japan, JCRB)

and maintained in Dulbecco's Modified Eagle's Medium-High Glucose (Invitrogen) medium with 10% fetal bovine serum (FBS), 2 mM L-glutamine (Invitrogen), and 100 μg/mL penicillin-streptomycin (Invitrogen). Cells were cultured in a humidified atmosphere in 5% $CO_2$ at 37° C.

2-2. Cytotoxicity Assay

A well-known cytotoxicity assays in the art, for example, the assay described by Wang et al. can be performed to study the cytotoxicity of the pharmaceutical composition provided by the present invention. Huh7, HepG2 and Hep3B cell lines were respectively seeded in 96-well plates ($5\times10^3$ cells/well) and treated with 0.1% DMSO (control) or various concentrations of the compound represented by formula (1) for 24 hours. The number of viable cells was determined by MTT assay.

Figure 1A:
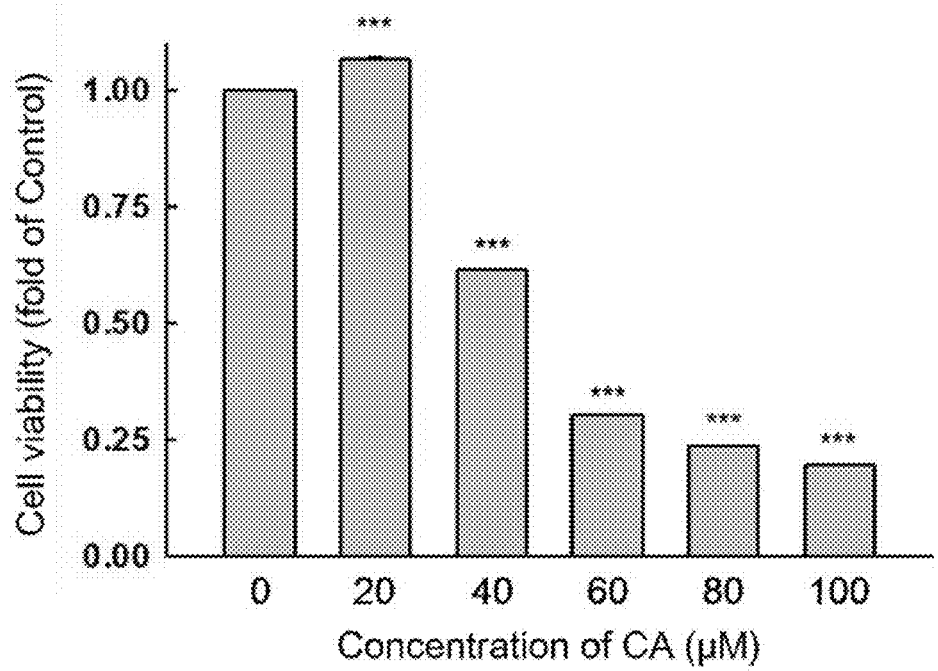
Figure 1B:
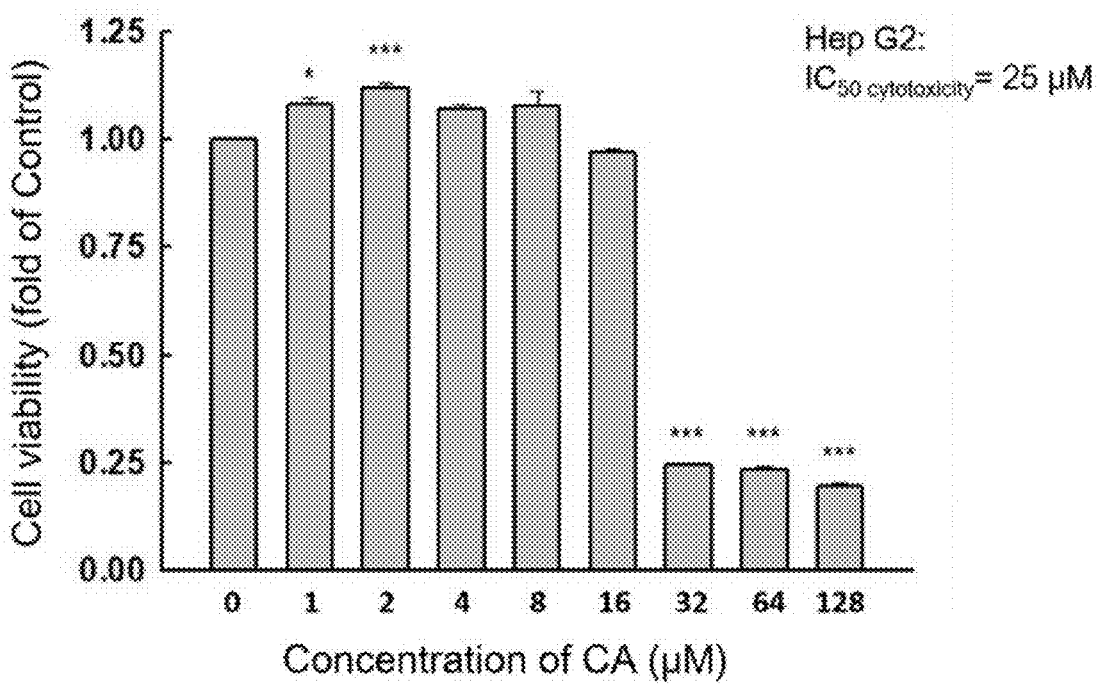
Figure 1C:
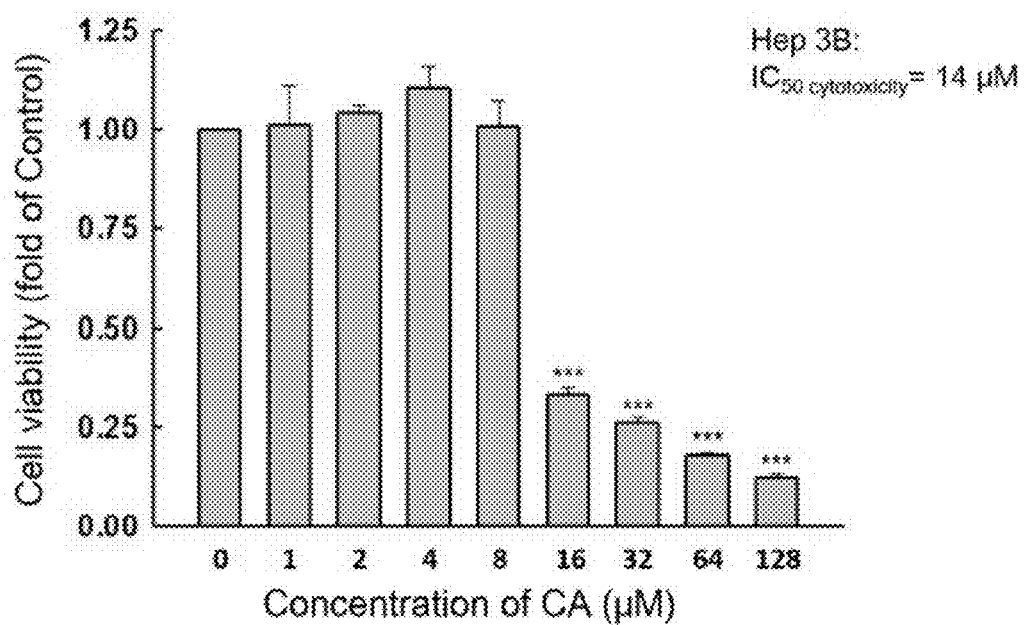

As shown in FIG. 1A, CA decreased the survival rate of Huh7 cell lines; the $IC_{50}$ of cytotoxicity was determined to be 50 μM. FIG. 1B further shows that CA has lower cytotoxicity to HepG2 and Hep3B cell lines.

Example 3: Evaluation of the Inhibitory Ability of CA to Cell Migration 3-1. Migration Assay Cells cultured by the method described in Example 2 were starved overnight ($5\times10^4$ cells) and resuspended in 300 μL serum-free DMEM medium with 0.1% DMSO (control) or various concentrations of compounds. Then, the cells were seeded into Transwell inserts (8 μm pore; BD Biosciences). The mediums were incubated for 16 hours, and the migrated cells were fixed, stained with crystal violet, and quantified.

Figure 2A:
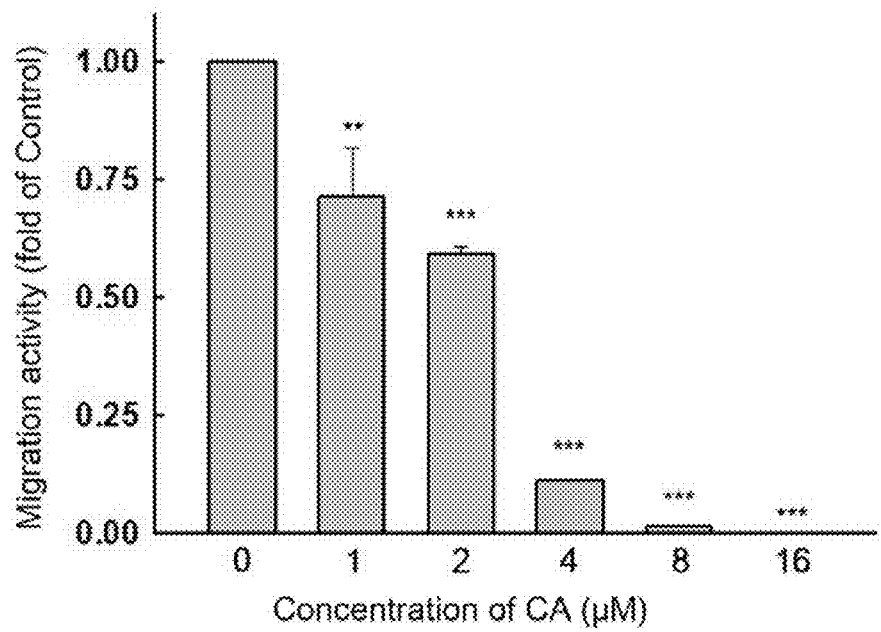
Figure 2B:
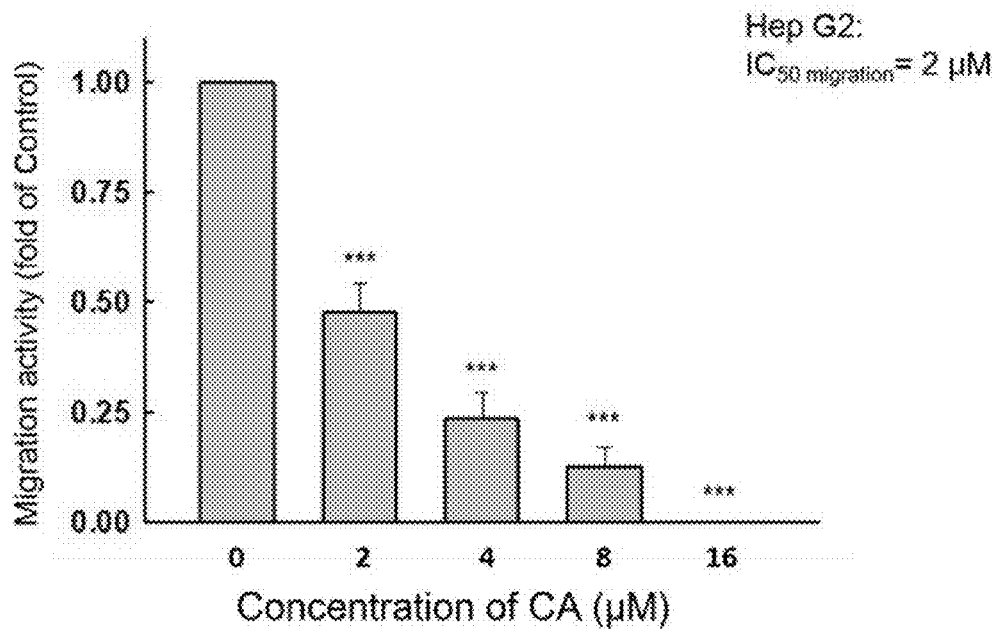
Figure 2C:
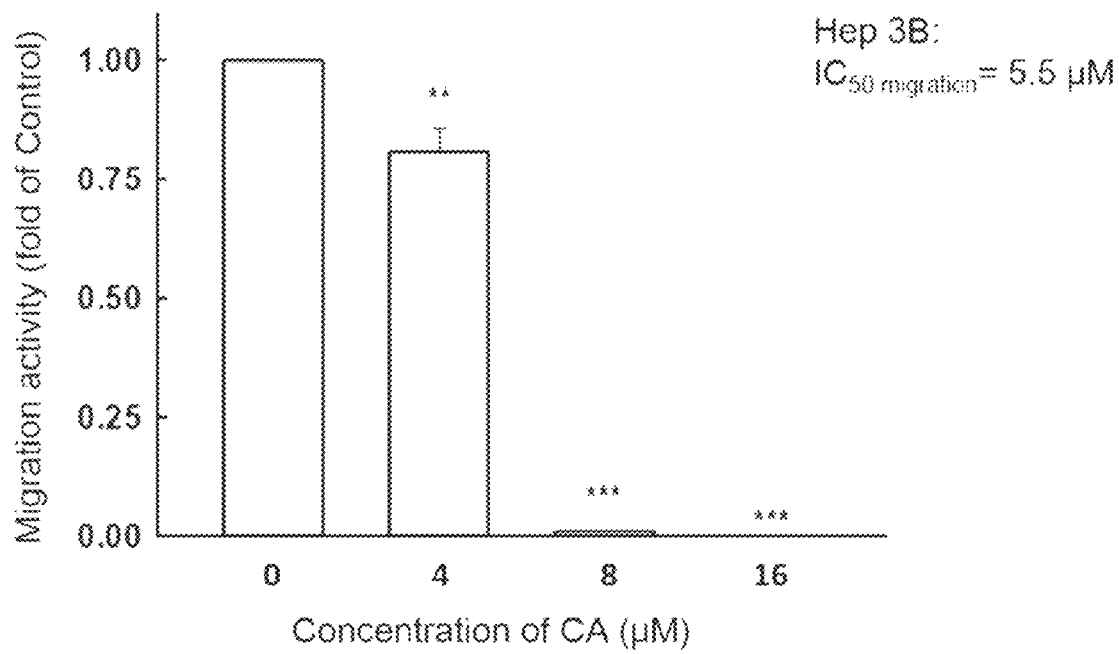

FIGS. 2A to 2C show that CA effectively inhibited the migration of Huh7, HepG2 and Hep3B cell lines. With increasing the concentration of CA, the inhibition was more significant. The specific concentration of CA can be 1 μM, 2 μM, 4 μM, 8 μM or 16 μM, each of which exhibited inhibitory activity to the migration of different HCC cell lines. In addition, the pharmaceutical composition inhibited the migration of HepG2 and Hep3B cell lines at low concentration.

Figure 2D:
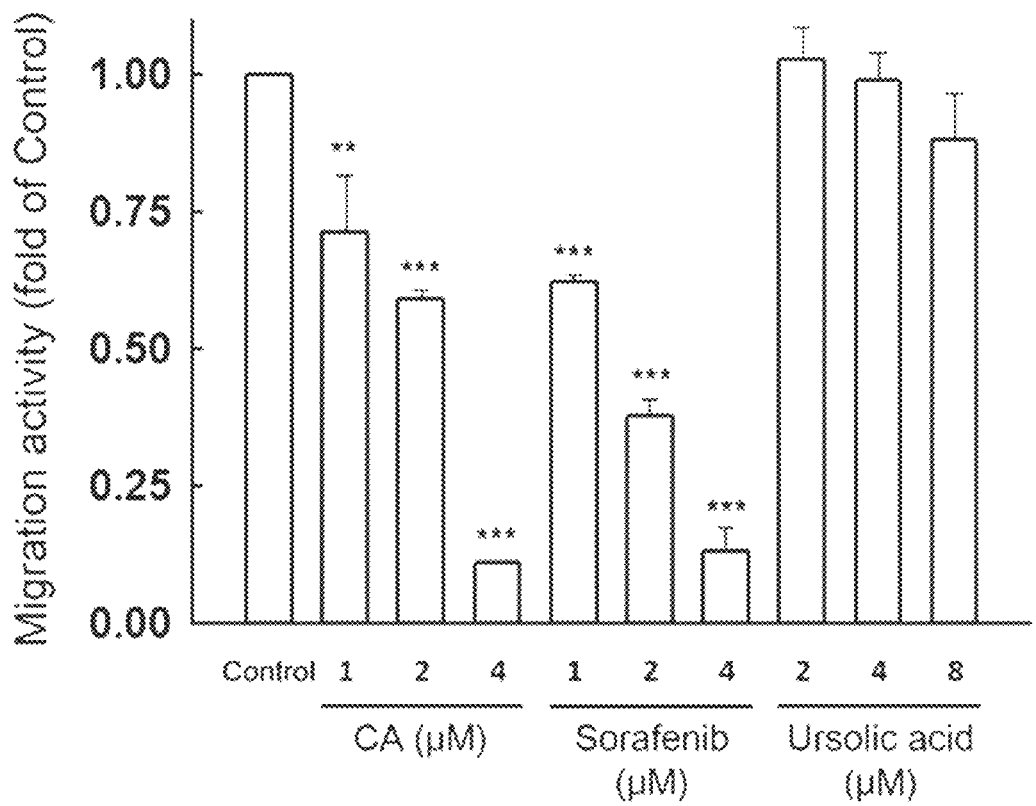

As shown in FIG. 2D, the inhibitory activity of CA to cell migration was similar to sorafenib, which means the effect of CA on inhibition of cell migration is equivalent to that of known anticancer agent, sorafenib. However, previous study [8] has reported that even though ursolic acid (3β-hydroxyurs-12-ursen-28-ic acid) has similar chemical structure with CA and can reduce the occurrence rate of cancer, ursolic acid did not show significant inhibitory activity to Huh7 cell lines migration.

According to the cytotoxicity assay, CA provided by the present invention has low cytotoxicity to HCC cell lines but has a relative high inhibitory effect on HCC cell lines migration. According to the equation, $IC_{50\ cytotoxicity}/IC_{50\ migration} \geq 20$, CA has low cytotoxicity and high inhibitory activity to cell migration.

3-2. Immunoprecipitation and Western Blot Analysis

Huh7 cell lines were cultured by the method described in Example 2 and treated with 0.1% DMSO (control) or various concentrations of CA for 15 mins and then lysed in RIPA buffer solution. The lysates were then sonicated and centrifuged. The supernatant was kept and incubated with anti-VEGFR1 antibody, anti-VEGFR2 antibody, and anti-VEGFR3 antibody (Santa Cruz Biotechnology, Inc.) overnight at 4° C. The immune-complexes were washed and eluted, and then analyzed by Western blotting.

Figure 3A:
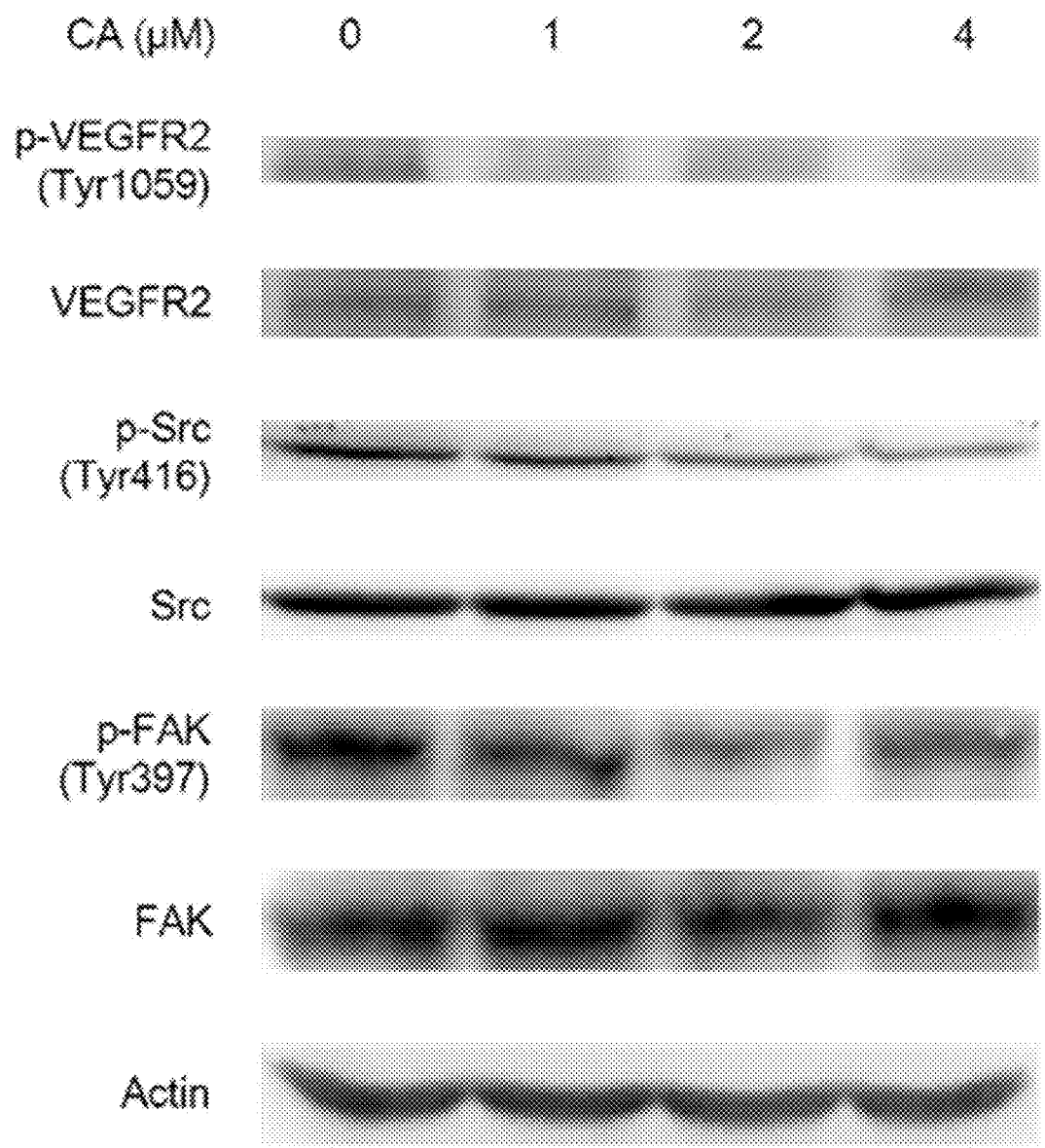
FIGS. 3A to 3D illustrate the phosphorylation level and normalized intensity of VEGFR2, Src and FAK of Huh7 cell lines treated with CA and analyzed by Western blot (* indicates P<0.5 indicates ** P<0.01 as compared with the control group).
Figure 3B:
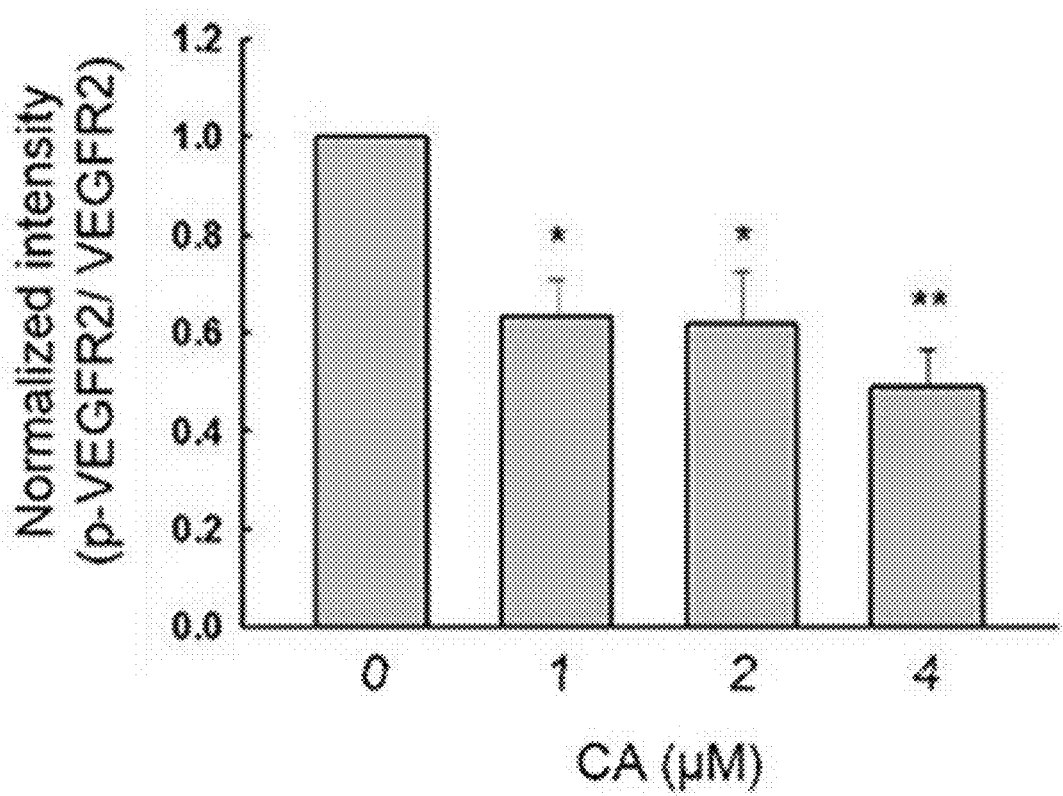
Figure 3C:
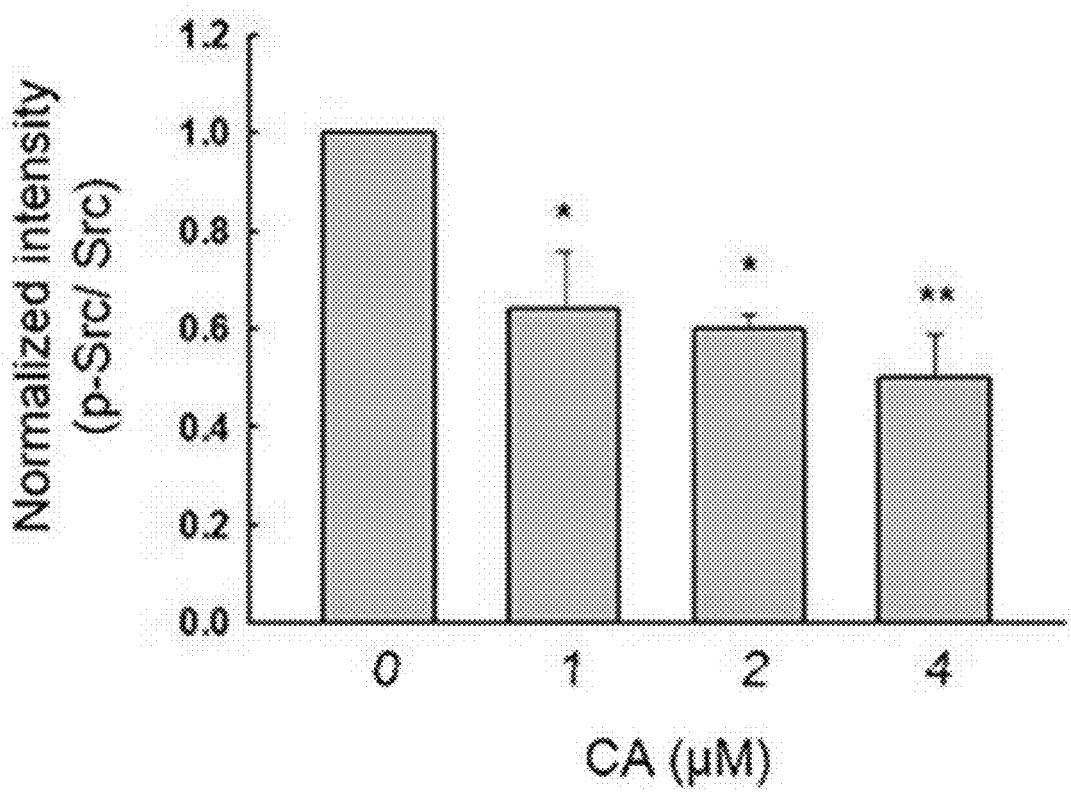
Figure 3D:
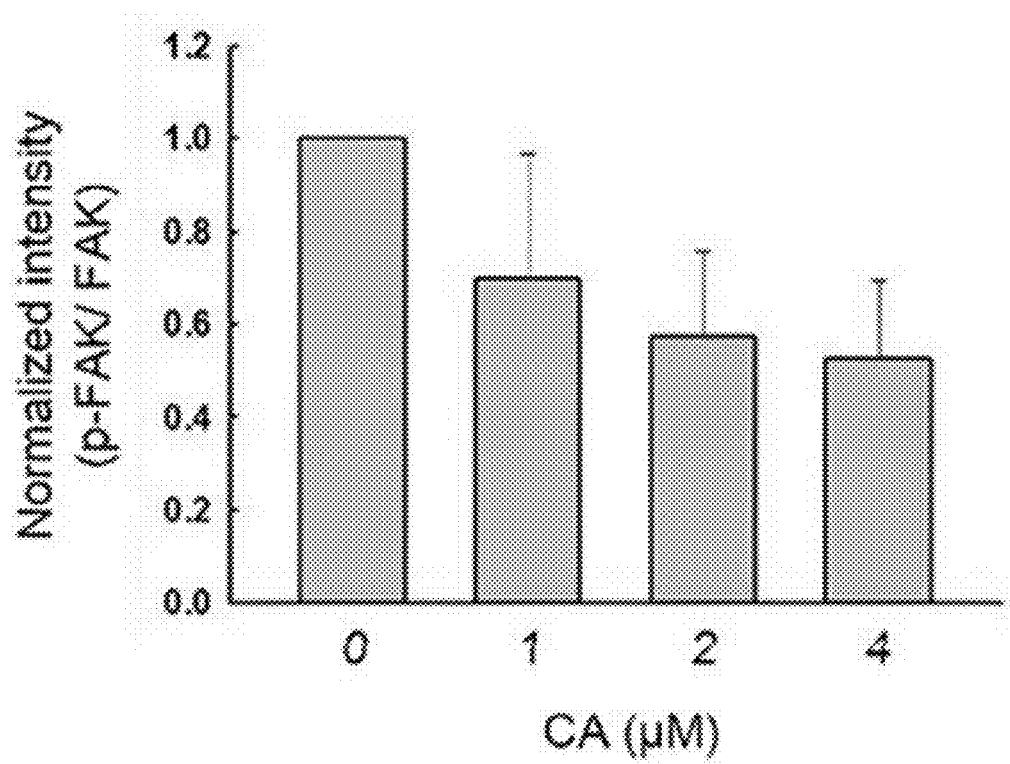

As shown in FIGS. 3A and 3B, the phosphorylation level of VEGFR2 was lower in treatment with CA than that of in control. The phosphorylation level of non-receptor tyrosine kinase, Src, and focal adhesion kinase, FAK (Tyr397), were also down-regulated by CA. It was reported previously that focal adhesion kinase (FAK) is activated by membrane receptors and then the Src/FAK complex modulates cell migration and actin rearrangement via Rho-GTPase pathways. Therefore, CA can significantly reduce phosphorylation of VEGFR2 and inhibit Src and FAK, and further inhibit cell migration.

3-3. Kinase Activity Assay

Figure 4:
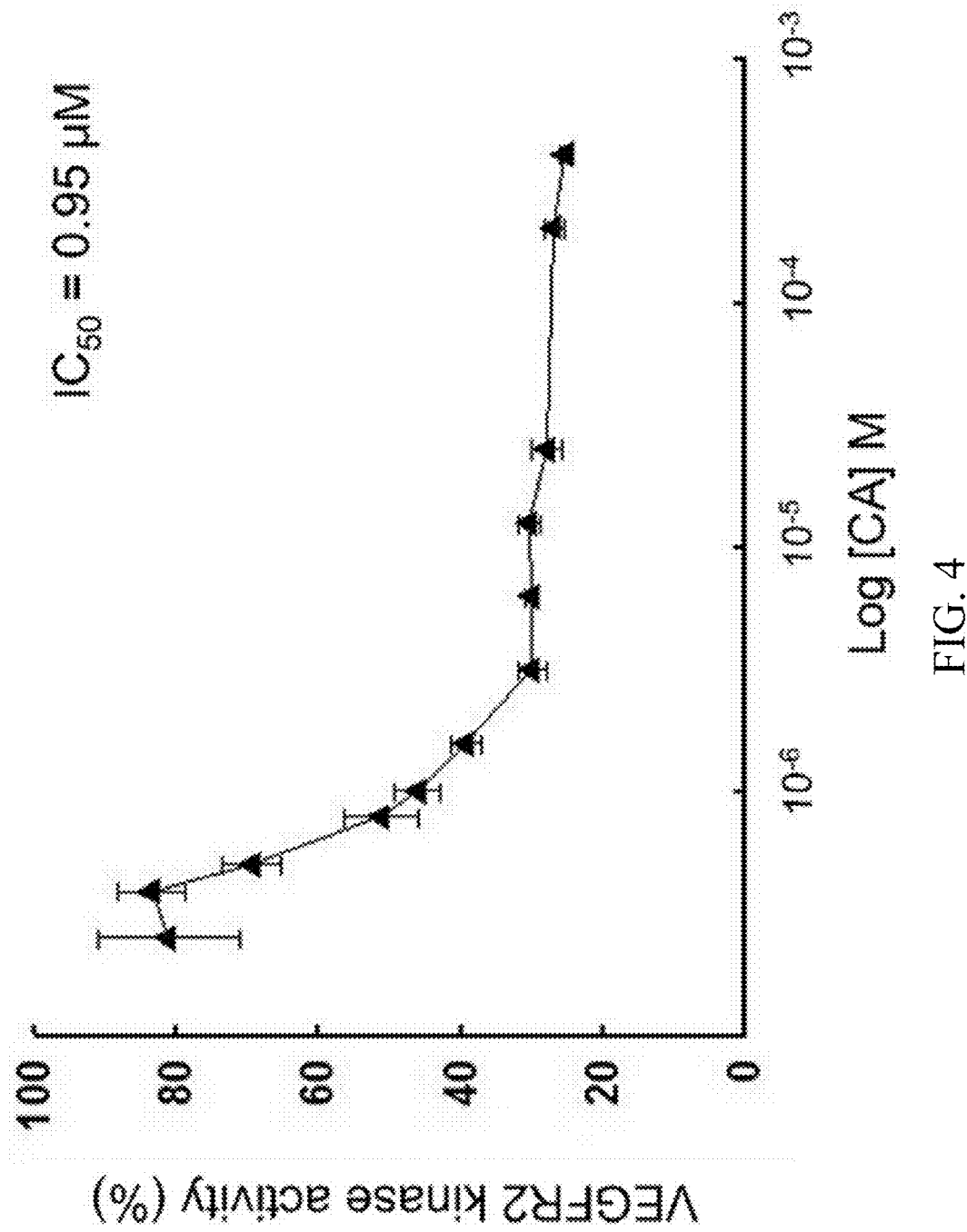
FIG. 4 illustrates the inhibitory effect of CA on VEGFR2 kinase activity assessed by ADP-Glo Kinase Assay.

The effect of the compound represented by formula (1) provided by the present invention on kinase Activity was evaluated and the experiment was performed with known kits, for example, the ADP-Glo kinase assay kit (Promega, Wis., USA). Briefly, CA was first diluted with a kinase reaction buffer solution at a 1:2 dilution ratio. Three nanograms of kinase insert domain receptor (KDR, #V2681, Promega) were added and incubated for 10 mins. Then, 0.1 μg/μL substrate and 10 μM ATP were added and incubated for 1 hour at room temperature. Next, 25 μL of ADP-Glo reagent was added to the mixture and incubated at room temperature for 40 mins. Finally, 50 μL of a kinase detection reagent was added to introduce luciferase and samples were measured. As shown in FIG. 4, it is found that about 0.95 μM of CA inhibited VEGFR2 activity by 50%.

3-4. Rho GTPase Activity Assay

Huh7 cell lines were cultured by the method described in Example 2 and treated with 0.1% DMSO (control) or CA for 6 hours and then collected. After the Huh7 cell lines were lysed, the cell lysates (500 μg) were combined with purified GST fusion protein which has conjugated with Rac1, RhoA, or cdc42 binding domain (PAK-PBD for Rac1 and cdc42, Raf-RBD for RhoA) and incubated at 4° C. overnight. The immune-complex was precipitated and then centrifuged at 14,000 rpm for 30 mins. The samples were washed with RIPA buffer solution, boiled with SDS sample buffer solution, and analyzed by Western blot analysis.

Figure 5A:
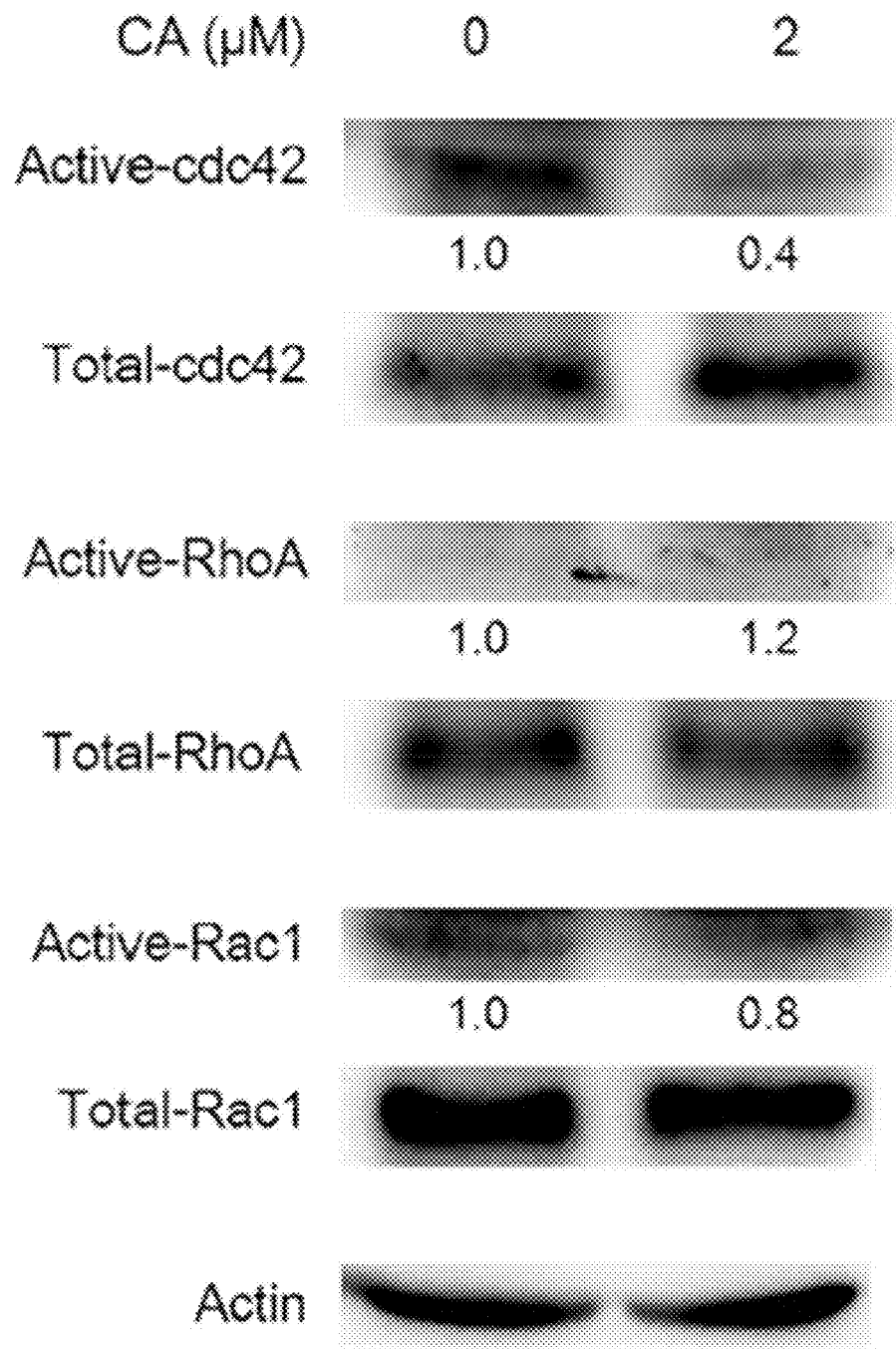
FIGS. 5A and 5B illustrate the effect of CA on the Rho-GTPase activity of Huh7 cell lines examined with GST pull-down assay and Western blot.
Figure 5B:
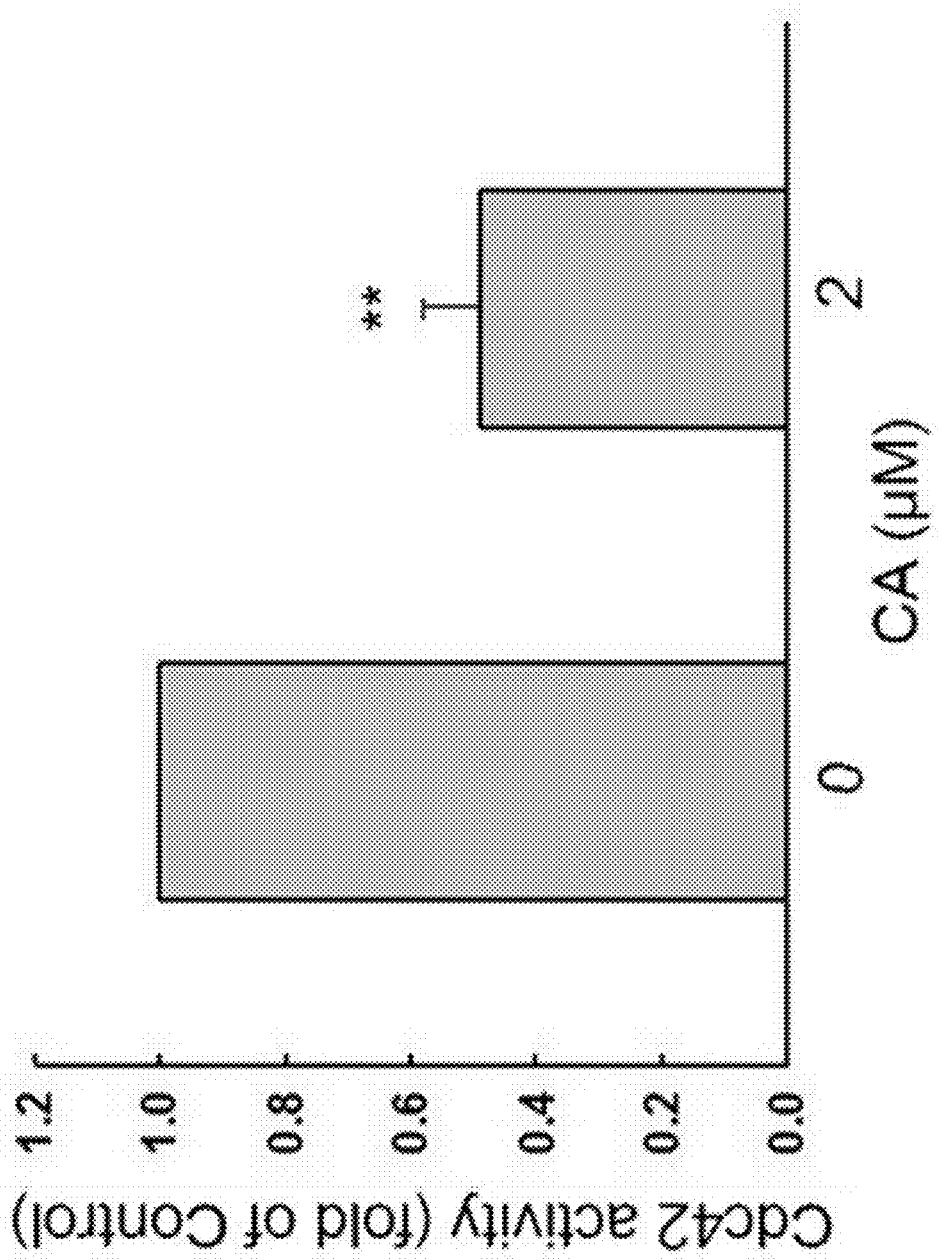

As sown in FIG. 5A, activated cdc42, but not Rac1 and RhoA, is significantly down-regulated by CA treatment. According to FIG. 5B, the data demonstrated that 2 μM of CA treatment reduces the activity of cdc42 by 50%. Recent studies have revealed that cdc42 may play an important role in the dynamic change of actin and the formation of filopodia during cell migration.

3-5. G-Actin/F-Actin Activity Assay

Actin activity assay can be conducted by known methods, for example, the method described in Shum et al. (2011). Briefly, Huh7 cell lines were cultured by the method described in Example 2 and treated with 0.1% DMSO (control) or CA for 6 hours and incubated in stabilizing buffer (1% Triton X-100, 1 μg phalloidin, and protease inhibitor cocktail) at room temperature for 5 mins. Cell lysates were collected, followed by centrifugation at 100,000×g at 37° C. for 1 hour. The supernatant was removed and saved as the G-actin fraction. The pellet was washed twice with PBS and dissolved in dissolving buffer solution (1% Triton X-100, 2% SDS, and protease inhibitor cocktail) by sonication, the mixture was put on ice for 1 h, and saved as the F-actin fraction.

Figure 6A:
FIGS. 6A and 6B illustrate the effect of CA on the expressions of F-actin or G-actin and the fractions of F-actin and G-actin.
Figure 6B:
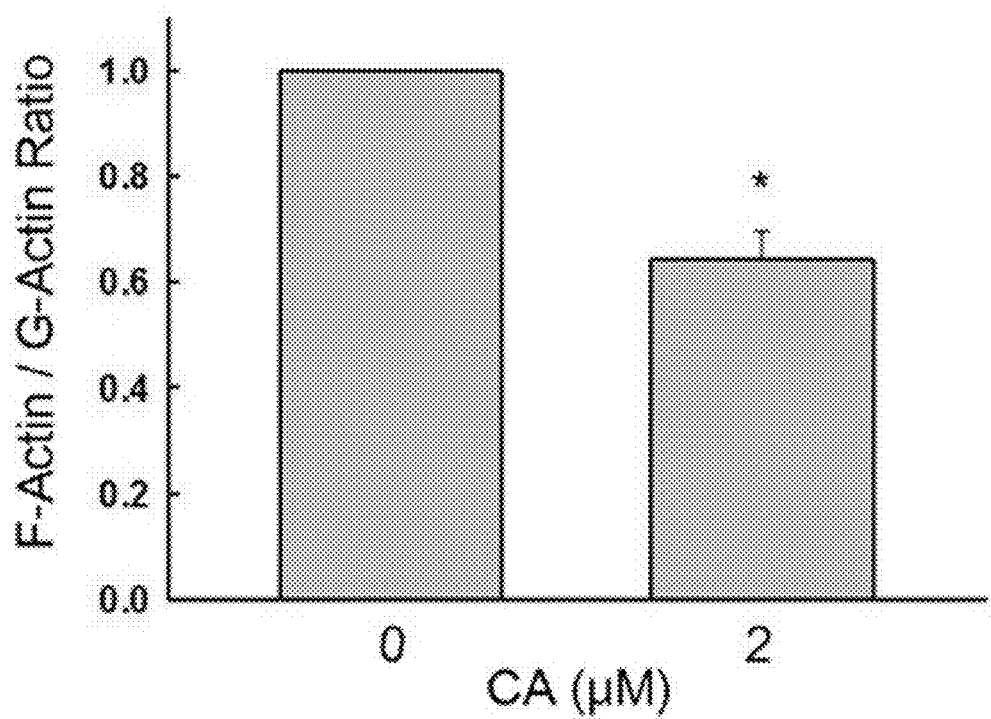

As shown in FIGS. 6A and 6B, it demonstrated that CA treatment reduces the ratio of F-actin/G-actin (polymer/monomer) as compared with the control group.

3-6. Confocal Microscopy Analysis

Huh7 cell lines cultured by the method described in Example 2 were seeded on a 22×22 cover slip and treated with 0.1% DMSO (control) or CA for 6 hour. The cells were washed, fixed, and permeabilized with 0.25% Triton X-100 for 10 mins. Next, the cover slips were incubated with p-FAK (Tyr397) primary antibody overnight, and then stained with Alexa488 (anti-rabbit) and Alexa568-phallodin (20 mU/mL) for 1 hour in darkness. Finally, the samples were counterstained for nuclei with DAPI (10 ng/mL) for 10 mins. The images were captured and analyzed using the Leica TCS SP5 Spectral Confocal System. The actin filament intensity was measured by ImageJ (NIH) and calculated by the following formula described by Bennett et al. (2013): Corrected total cell fluorescence (CTCF)=Integrated Density−(Area of selected cell×Mean fluorescence of background readings).

Figure 7A:
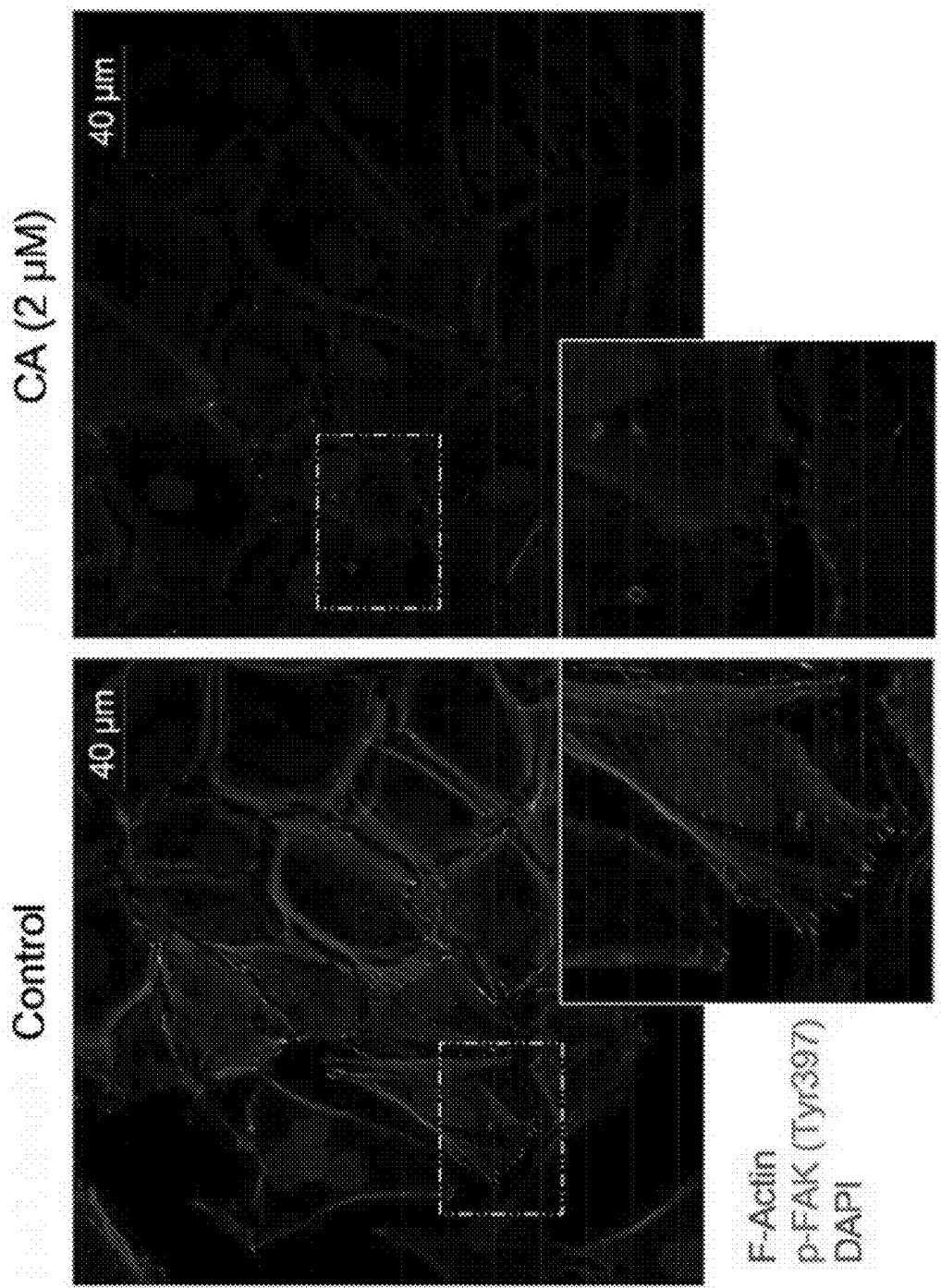
FIGS. 7A and 7B illustrate the immunocytochemistry staining of Huh7 cell lines treated with or without CA. The phalloidin-stained Factin (red) and p-FAK (green) co-localized at the leading edge of cells of the control group.
Figure 7B:
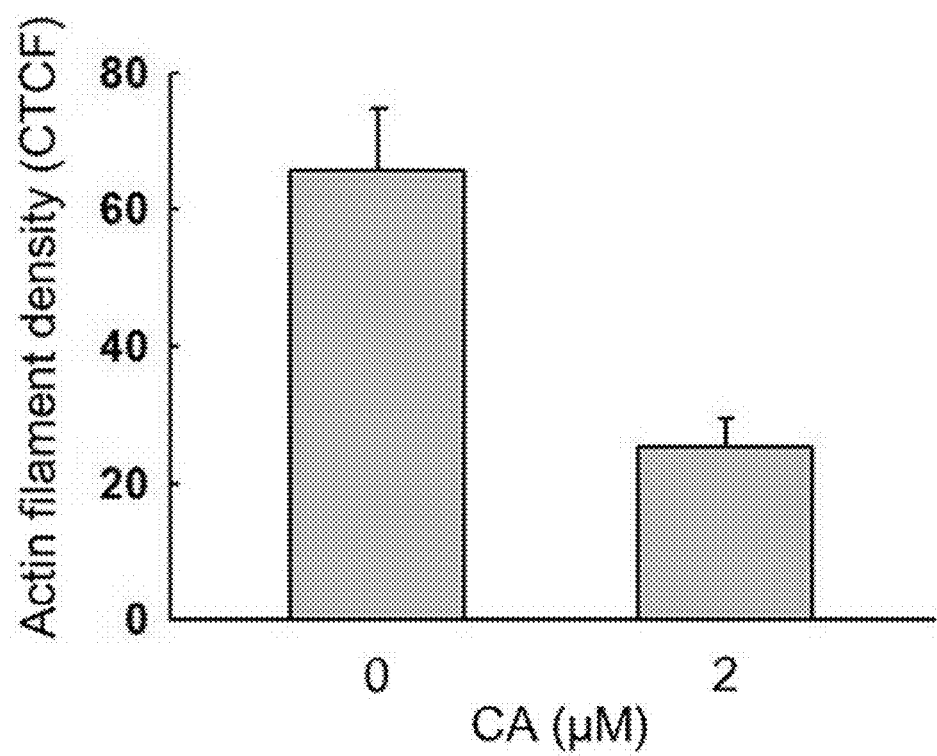

FIG. 7A shows that CA decreases the co-localization of phosphorylation of FAK (Tyr397) and F-actin on the filopodium (leading edge) in Huh7 cell lines.

VEGFR2 is the major receptor in the VEGF signaling pathway which regulates cell migration, proliferation, and angiogenesis. It is activated by VEGF binding, leading to trans/auto phosphorylation of intracellular tyrosine residues. The residues Tyr1054 and Tyr1059, located in the active loop of the kinase domain, are relevant critical for VEGFR2 kinase activity. The phosphorylation of Tyr1054 and Tyr1059 can induce downstream signal transduction, including Src and FAK [9, 10].

According to the examples above, it can demonstrates that CA provided by the present invention reduces the tyrosine phosphorylation level of VEGFR2, and CA can inhibit the activation of Src, FAK and cdc42, which results in suppressing the VEGFR2/Src/FAK/cdc42 signaling pathway and actin remodeling and further inhibit the migration of HCC cell lines.

Example 4: Animal Model 4-1. Antitumor Response In Vivo

All animal experiments were conducted according to the guidelines approved by the Institutional Animal Care and Use Committees of the College of Medicine, National Taiwan University and National Taiwan Normal University. The study was approved by the Animal Care and Use Committees of the College of Medicine, National Taiwan University and National Taiwan Normal University. Male NOD/SCID mice (4-6 weeks old) (obtained from BioLASCO Taiwan Co., Ltd) were housed into individually-ventilated cages with free access to food and drinking water.

Huh7 cell lines ($2\times10^6$ cells) were suspended in 200 μL of Opti-MEM (Invitrogen) and injected subcutaneously into the flanks of each mouse. After one week, the mice were treated with 50 μL DMSO (control) or CA (5 mg/kg/day) by intraperitoneal injection (n=5 for each group) for 21 days.

To study the combinatorial effect of CA and sorafenib, Huh7 cell lines ($5\times10^6$ cells) were suspended in 100 μL of Opti-MEM with matrigel-matrix, and injected subcutaneously into the flanks of each mouse. After one week, the mice were treated with 50 μL DMSO (control) and combined compounds by intraperitoneal injection (n=5 for each group) for 20 days.

The tumor volume was calculated by the following equation:

$$\text{tumor volume(mm}^3\text{)=(length [mm])}\times\text{(width [mm])}^2\times 0.5.$$

At the end of the experiment, the mice were sacrificed. The tumors were excised, weighed, and fixed for further studies.

FIGS. 8A and 8B show the difference of the tumors in mice with different treatments. It can be observed that after 21-day treatment, the volumes of the tumor in CA-treated group were $63\pm19$ mm$^3$, which much smaller than that of control group ($669\pm67$ mm$^3$). In addition, the CA-treated group showed 85% reduction in tumor mass as compared with the control group. FIG. 8C shows that body weights of mice treated with CA were similar to that of control group, which suggest that the dosage of CA administered had insignificant toxic effects to the mice.

4-2. Immunohistochemistry

Tumor samples obtained from experiment 4-1 were fixed in 10% Trioxane, embedded in paraffin, and sectioned. The tissue sections were then subjected to immunohistochemical staining with the Novolink Polymer Detection System (Leica Biosystems). The sections were stained for p-VEGFR2 (Tyr951, Cell Signaling Technology), Ki-67 and p-FAK (Tyr397) (Santa Cruz Biotechnology), and the nuclei were counterstained with hematoxylin.

FIG. 9 shows the surgical biopsy of tumor lesions in the mice of experiment 4-1. It can be observed that CA reduced phosphorylation of both VEGFR2 and FAK significantly in HCC xenograft mice.

Example 5: Synergistic Analysis

Except for the compound represented by formula (1), the pharmaceutical composition can further comprises at least one known anticancer agent. The synergistic effect of the compound represented by formula (1) and the known anticancer agent can be evaluated by known methods, for example it can be analyzed by the Compusyn software, which is developed by Chou and Martin [11]. The software was used to estimate the combination index (CI) and Fa (fraction affected by drugs) and to interpret the combined effect of drugs. CI<1, CI=1, and CI>1 respectively indicate synergistic, additive, and antagonistic effects.

The use of the pharmaceutical composition of the present invention in combination with a multikinase inhibitor which is used as an anticancer agent is preferable, wherein the anticancer agent can be sorafenib, brivanib, bevacizumab, linifanib, pazopanib, vatalanib, cediranib, ramucirumab, TSU-68, vandetanib, foretinib, sunitinib, etc.

Sorafenib (Nexavar®) is one of anticancer agents inhibiting VEGFR2/3, PDGFRβ and Flt-3 for treating HCC, and has been approved by FDA.

5-1. Synergistic Effect on Cell Migration and Antitumor Activity In Vivo

The experiment was based on the method described in Examples 3 and 4 to evaluate the synergistic effect of the combination of the compound represented by formula (1) provided by the present invention and a known anticancer agent on inhibiting cell migration and antitumor activity in vivo.

FIG. 10A shows the combinatorial effects of CA and sorafenib. The result demonstrated that CA had a synergistic effect with sorafenib on Huh7 cell lines migration at a molar ratio of 1:4 to 1:1. Besides, Table 1 shows that the combination use of CA and sorafenib also had synergistic effect on inhibiting cell migration of HepG2 and Hep3B cell lines.

TABLE 1

| HepG2 | | | | Hep3B | | | |
| --- | --- | --- | --- | --- | --- | --- | --- |
| Sorafenib (μM) | CA (μM) | (Fa) | (CI) | Sorafenib (μM) | CA (μM) | (Fa) | (CI) |
| 2.0 | 2.0 | 0.49 | 6.99 | 5.0 | 5.0 | 0.94 | 0.44 |
| 2.0 | 4.0 | 0.65 | 0.95 | 10.0 | 5.0 | 0.97 | 0.34 |
| 4.0 | 2.0 | 0.71 | 1.21 | 5.0 | 10.0 | 0.97 | 0.65 |
| 4.0 | 4.0 | 0.87 | 0.68 | 10.0 | 10.0 | 0.99 | 0.50 |

According to FIGS. 10B to 10D, it reveals that CA enhanced sorafenib-mediated inhibition of phosphorylation of VEGFR2, Src, and FAK. FIGS. 10E and 10F show the effect of combined treatment with CA and sorafenib on the xenograft model. It was observed that combined treatment with CA and sorafenib had a synergistic effect on inhibiting tumor growth in mice, wherein the dosage of CA can be more than 0 to 5 mg/kg/day, whereas the dosage of sorafenib can be more than 0 to 20 mg/kg/day. These results demonstrated the combination of CA and sorafenib is useful for the treatment of HCC, and the administered concentration is non-toxic to subjects.

FIGS. 10G to 10I show that combined treatment with CA and sorafenib down-regulated the phosphorylation level of Src and FAK kinases in the tumor in the mice. However, sorafenib alone didn't show any inhibitory effect to the activation of FAK kinase in the xenograft model.

5-2. SRB Cell Growth Assay

Three HCC cell lines, Huh7, HepG2, and Hep3B, were seeded into 96-well plates ($5 \times 10^3$ cells/well) and treated with 0.1% DMSO (control) or various concentrations of CA and sorafenib. After 24 hours, cells were fixed with 10% TCA and stained with sulforhodamine b (SRB) at 0.4% (w/v) in 1% acetic acid. The cells were then washed by 1% acetic acid, solubilized with 10 mM Tris base solution, and measured the absorbance by ELISA reader (515 nm wavelength).

As shown in FIGS. 11A to 11C, the combination use of CA and sorafenib showed synergistic effect on the growth of HCC cell lines.

These results demonstrate a synergistic interaction between the compound represented by formula (1) provided by the present invention and the known anticancer agent in the inhibition of the growth of HCC cells and the treatment for HCC.

Example 6: Molecular Docking

The interaction of CA and the ATP-binding site in VEGFR2 (PDB id: 1YWN) was illustrated by Discovery Studio Modeling 4.0 and displayed by PyMOL (ver. 1.6.0b1) in FIG. 12A. This analysis suggests that CA may bind to the ATP-binding cavity of the VEGFR2 kinase domain. Previous studies suggested that residues Glu883, Cys917, and Asp1044 of VEGFR2 may be involved in ligand binding through H-bond interactions [12]. As shown in FIG. 12B, CA potentially interacted with Glu883 at a distance of 2.67 Å. Additionally, CA also interacted with Val846, Lys866, Val897, Val914, and Cys1043. These interactions between CA and VEGFR2 kinase can result in inhibition of VEGFR2 and subsequent downstream intracellular signaling.

The ATP binding pocket in the VEGFR2 catalytic domain bound CA with lower binding energy than ATP, which are −15.2 kcal/mol and −12.3 kcal/mol, respectively. Moreover, the surface charge distribution of VEGFR2 demonstrated that the OH groups of CA interact with the ATP binding pocket stably. It also revealed that most uncharged areas of CA can generate hydrophobic forces with valine and cysteine and stabilizes the binding affinity thereby. It strongly suggests that the binding of CA to the ATP-binding pocket of VEGFR2 can mediate the down-regulation of VEGFR2 phosphorylation and subsequent signals.

To Sum up, the pharmaceutical composition provided by the present invention presents anticancer activity against HCC in vitro or in vivo. Specifically, the pharmaceutical composition can block the downstream Src/FAK/cdc42 signaling pathway by blocking ATP binding site of VEGFR2 to inhibit the activity of VEGFR2 kinase, which further disrupt actin filament formation. The pharmaceutical composition has an inhibitory activity against cell migration and antitumor effects in a xenograft model. Moreover, due to the low cytotoxicity of the pharmaceutical composition provided by the present invention, the pharmaceutical composition can be used as a novel VEGFR2 inhibitor for HCC therapy. Alternatively, the use of the pharmaceutical composition of the present invention in combination with existing anticancer agents can be an adjuvant therapy due to the synergistic effect resulted therefrom.

The principles and effects of the present invention have been described using the above examples, which are not used to limit the present invention. Without departing from the spirit and scope of the present invention, any one skilled in the art can modify the above examples. Therefore, the scope of the present invention should be accorded with the claims appended.

The literatures cited by the present application are listed below, and each of the references is incorporated herein by reference.

REFERENCES

The references cited herein are listed below, and each of which is hereby incorporated herein by reference respectively.

1. Olsson A K, Dimberg A, Kreuger J, Claesson-Welsh L., "VEGF receptor signalling—in control of vascular function," *Nat. Rev. Mol. Cell Biol.*, 2006, 7(5):359-371; PMID: 16633338
2. Claesson-Welsh L, Welsh M., "VEGFA and tumour angiogenesis," *J. Intern. Med.*, 2013, 273(2):114-127; doi: 10.1111/joim.12019 PMID: 23216836
3. Lamalice L, HouleFo, Huot J., "Phosphorylation of Tyr1214 within VEGFR-2 Triggers the Recruitment of Nck and Activation of Fyn Leading to SAPK2/p38 Activation and Endothelial Cell Migration in Response to VEGF," *J. Biol. Chem.*, 2006, 281(45):34009-34020; PMID: 16966330
4. Zhang L, Wang J N, Tang J M, Kong X, Yang J Y, Zheng F, et al., "VEGF is essential for the growth and migration of human hepatocellular carcinoma cells," *Mol. Biol. Rep.*, 2012, 39(5):5085-5093; doi: 10.1007/s11033-011-1304-2 PMID: 22161247
5. Lee K, Jeong K W, Lee Y, Song J Y, Kim M S, Lee G S, et al., "Pharmacophore modeling and virtual screening studies for new VEGFR-2 kinase inhibitors," *Eur. J. Med. Chem.*, 2010, 45(11):5420-5427; doi: 10.1016/j.ejmech.2010.09.002 PMID: 20869793
6. Llovet J M, Ricci S, Mazzaferro V, Hilgard P, Gane E, Blanc J F, et al., "Sorafenib in advanced hepatocellular carcinoma," *N. Engl. J. Med.*, 2008, 359(4):378-390; doi: 10.1056/NEJMoa0708857 PMID: 18650514
7. Zhu A X, Duda D G, Sahani D V, Jain R K, "HCC and angiogenesis: possible targets and future directions," *Nat.*

Rev. Clin. Oncol., 2011, 8(5):292-301; doi: 10.1038/nrclinonc.2011.30 PMID: 21386818
8. Kim J H, Kim Y H, Song G Y, Kim D E, Jeong Y J, Liu K H, et al., "Ursolic acid and its natural derivative corosolic acid suppress the proliferation of APC-mutated colon cancer cells through promotion of β-catenin degradation," *Food Chem. Toxicol.*, 2014, 67:87-95; doi: 10.1016/j.fct.2014.02.019 PMID: 24566423
9. Matsumoto T, Claesson-Welsh L., "VEGF receptor signal transduction," *Sci. STKE*, 2001, 2001(112):re21; PMID: 11741095
10. Roskoski R, Jr., "VEGF receptor protein-tyrosine kinases: structure and regulation," *Biochem. Biophys. Res. Commun.*, 2008, 375(3):287-291; doi: 10.1016/j.bbrc.2008.07.121 PMID: 18680722
11. Gottwein J M, Jensen S B, Li Y P, Ghanem L, Scheel T K H, Serre S B N, et al. "Combination treatment with hepatitis C virus protease and NS5A inhibitors is effective against recombinant genotype 1a, 2a, and 3a Viruses," *Antimicrob. Agents Chemother.*, 2013, 57(3):1291-1303; doi: 10.1128/AAC.02164-12 PMID:23274664
12. Lee K, Jeong K W, Lee Y, Song J Y, Kim M S, Lee G S, et al., "Pharmacophore modeling and virtual screening studies for new VEGFR-2 kinase inhibitors," *Eur. J. Med. Chem.*, 2010, 45(11):5420-5427; doi: 10.1016/j.ejmech.2010.09.002 PMID: 20869793

What is claimed is:
1. A pharmaceutical composition, comprising:
a therapeutically efficient amount of a compound represented by formula (1),

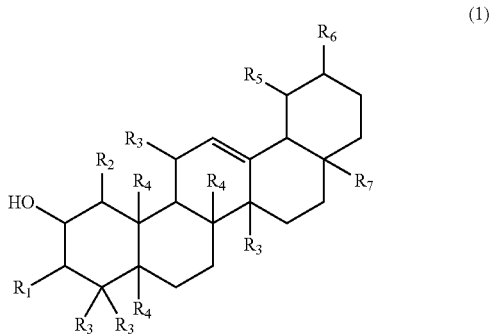

wherein
R$_1$ is H, hydroxy, or methyl;
R$_2$ is H, C$_1$-C$_3$alkyl, hydroxy, —CN or halogen;
each of R$_3$ and R$_4$ is independently selected from the group consisting of H, C$_1$-C$_3$alkyl, hydroxy, —CN, and halogen;
R$_5$ is H, hydroxy or methyl;
R$_6$ is H, C$_1$-C$_3$alkyl, hydroxy, —CN, halogen, or —COOR$_{11}$; and
R$_7$ is C$_1$-C$_3$alkyl or —COOR$_{11}$, wherein R$_{11}$ is H or C$_1$-C$_3$alkyl;
at least a multikinase inhibitor, wherein the molar ratio of the compound and the at least a multikinase inhibitor in the pharmaceutical composition is from 2:1 to 1:32; and
a pharmaceutically acceptable carrier.
2. The pharmaceutical composition of claim 1, wherein R$_1$ is hydroxy and each of R$_3$ and R$_4$ is independently selected from the group consisting of methyl, ethyl, and —CN.

3. The pharmaceutical composition of claim 1, wherein the compound is represented by formula (2),

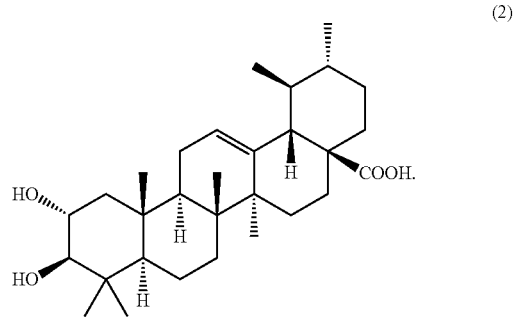

4. The pharmaceutical composition of claim 1, wherein the concentration of the compound is from 1 μM to 50 μM.
5. The pharmaceutical composition of claim 1, wherein the multikinase inhibitor is sorafenib.
6. The pharmaceutical composition of claim 1, wherein the concentration of the at least a multikinase inhibitor is from 1 μM to 10 μM.
7. A method of treating hepatocellular carcinoma and/or inhibiting proliferation or migration of hepatocellular carcinoma cells, comprising contacting the hepatocellular carcinoma and/or the hepatocellular carcinoma cells with a medicament comprising at least an anticancer agent and a compound represented by formula (1):

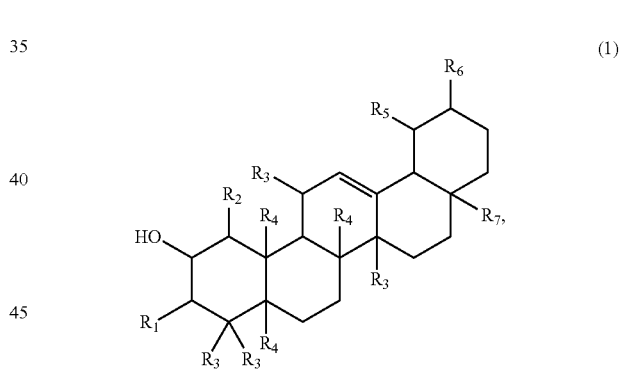

wherein
R$_1$ is H, hydroxy, or methyl;
R$_2$ is H, C$_1$-C$_3$alkyl, hydroxy, —CN or halogen;
each of R$_3$ and R$_4$ is independently selected from the group consisting of H, C$_1$-C$_3$alkyl, hydroxy, —CN, and halogen;
R$_5$ is H, hydroxy or methyl;
R$_6$ is H, C$_1$-C$_3$alkyl, hydroxy, —CN, halogen, or —COOR$_{11}$; and
R$_7$ is C$_1$-C$_3$alkyl or —COOR$_{11}$, wherein R$_{11}$ is H or C$_1$-C$_3$alkyl.
8. The method of claim 7, wherein R$_1$ is hydroxy and each of R$_3$ and R$_4$ is independently selected from the group consisting of methyl, ethyl, and —CN.
9. The method of claim 7, wherein the compound is represented by formula (2),

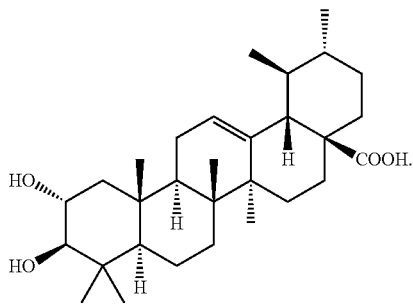
(2)

10. The method of claim 7, further comprising measuring expression or activity of a protein selected from the group consisting of VEGFR2 kinase, VEGFR2, Src, FAK, cdc42, RhoA, Rac 1, actin, and a combination thereof.

11. The method of claim 7, wherein a therapeutically efficient amount of the medicament administrated to a subject is from 2.5 mg to 5 mg of the compound represented by the formula (1) per kilogram of body weight.

12. The method of claim 7, wherein the at least an anticancer agent is a multikinase inhibitor.

13. The method of claim 12, wherein the multikinase inhibitor is sorafenib.

14. The method of claim 7, wherein the molar ratio of the compound and the at least an anticancer agent is from 2:1 to 1:32 in the medicament.

15. The method of claim 7, wherein a therapeutically efficient amount of the medicament administered to a subject is from 12.5 mg to 25 mg per kilogram of bodyweight, and a therapeutically efficient amount of the at least an anticancer agent is from 10 mg to 20 mg per kilogram of body weight.

16. A method of treating hepatocellular carcinoma and/or inhibiting proliferation or migration of hepatocellular carcinoma cells, comprising contacting the hepatocellular carcinoma and/or the hepatocellular carcinoma cells with a medicament comprising a compound represented by formula (2):

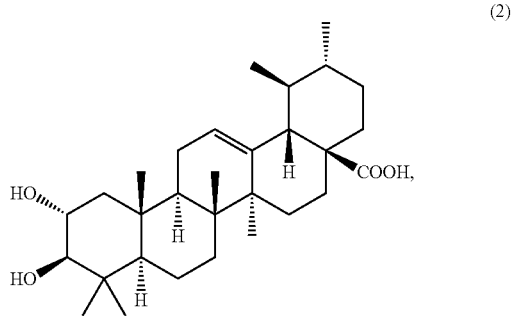
(2)

wherein the medicament further comprises at least an anticancer agent, and the molar ratio of the compound represented by formula (2) and the at least an anticancer agent is from 2:1 to 1:32 in the medicament.

17. The method of claim 16, wherein, the at least an anticancer agent is a multikinase inhibitor.

18. The method of claim 17, wherein the multikinase inhibitor is sorafenib.

* * * * *